United States Patent [19]
Kubota et al.

[11] Patent Number: 5,958,749
[45] Date of Patent: Sep. 28, 1999

[54] DNA ENCODING A POLYPEPTIDE POSSESSING MALTOTETRAOSE-FORMING AMYLASE ACTIVITY

[75] Inventors: Michio Kubota; Tetsuya Nakada; Shuzo Sakai, all of Okayama, Japan

[73] Assignee: Kabushiki Kaisha Hayashibara Seibutsu Kagaku Kenkyujo, Okayama, Japan

[21] Appl. No.: 07/860,583

[22] Filed: Mar. 27, 1992

Related U.S. Application Data

[62] Division of application No. 07/212,330, Jun. 27, 1988, abandoned.

[30] Foreign Application Priority Data

Jul. 8, 1987 [JP] Japan .................... 62-168524

[51] Int. Cl.⁶ .................. C12N 9/24; C12N 15/56; C12P 19/14
[52] U.S. Cl. ............... 435/200; 435/99; 435/320.1; 435/252.3; 536/23.2
[58] Field of Search .............. 435/200, 320.1, 435/252.3, 99; 536/23.2

[56] References Cited

U.S. PATENT DOCUMENTS

| | | |
|---|---|---|
| 3,654,082 | 4/1972 | Abdullah . |
| 3,832,285 | 5/1888 | Kurimoto . |
| 4,675,293 | 6/1987 | Gibs .................... 435/95 |
| 4,738,928 | 4/1988 | Weissman et al. ........... 435/172.3 |

FOREIGN PATENT DOCUMENTS

| | | |
|---|---|---|
| 0149915 | 12/1984 | European Pat. Off. . |
| 0257535 | 8/1987 | European Pat. Off. . |
| 4647 | of 1973 | Japan . |
| 102854 | of 1974 | Japan . |
| 148794 | of 1984 | Japan . |

OTHER PUBLICATIONS

Archives of Biochemistry and Biophysics, vol. 145, pp. 105–114 (1971).
Biochimica et Biophysica Acta., vol. 566, pp. 88–99 (1979).
Agricultural and Biological Chemistry, vol. 47, No. 8, pp. 1761–1768 (1983).
Bergey's Manual of Determinative Bacteriology, 7th Edition (1957)—front page and contents.
Bergey's Manual of Determinative Bacteriology, 8th Edition (1974)—front page and contents.
The Journal of Biological Chemistry, vol. 256, No. 15, pp. 7990–7997 (1981).
World Patent Index (WPI) by Dialog Information Service, Inc. (Dialog) (Attached to JAP 102854/74).
World Patent Index (WPI) by Dialog Information Service, Inc (Dialog) (Attached to JAP 148794/84).
Biochemica et Biophysica Acta, vol. 72, pp. 619–629 (1963).
Journal of Bacteriology, vol. 127, No. 3, pp. 1524–1537 (1976).
The Journal of Biological Chemistry, vol. 244, No. 16, pp. 4406–4412 (1969).
The Journal of Biological Chemistry, vol. 248, No. 7, pp. 2296–2302 (1973).
Applied and Microbiology Biotechnology, vol. 23, pp. 355–360 (1986).
Agricultural and Biological Chemistry, vol. 46, No. 3, pp. 639–646 (1982).
Patent Abstract of Japan, vol. 11, No. 30, JP–A–202 687 Shokuhin Sogo Kenkyusho, Aug. 9, 1986.
Patent Abstracts of Japan, vol. 11, No. 261, JP–A–62 134 088 Shokuhin Sangyo Baioriakutaa Syste Gijutsu Kenkyu Kumiai, Jun. 17, 1987.

*Primary Examiner*—Keith D. Hendricks
*Attorney, Agent, or Firm*—Browdy and Neimark

[57] ABSTRACT

A polypeptide possessing maltotetraose-forming amylase activity with a revealed amino acid sequence. The polypeptide has features that it acts on starch to mainly produce maltotetraose, and that it has a molecular weight of $50,000 \pm 10,000$ when electrophoresed on SDS-polyacrylamide gel.

The polypeptide can be advantageously used in industrial process.

16 Claims, 2 Drawing Sheets

DNA ENCODING A POLYPEPTIDE POSSESSING MALTOTETRAOSE-FORMING AMYLASE ACTIVITY

This appication is a divisional of application Ser. No. 07/212/330, filed Jun. 27, 1988, now abandoned.

BACKGROUND OF THE INVENTION

FIELD OF THE INVENTION

The present invention relates to a polypeptide possessing maltotetraose-forming amylase activity, and its uses.

ABBREVIATIONS

In the specification, amino acids, peptides, etc., may be represented by abbreviations commonly used in the art. Some of such abbreviations are given in the below. Optical isomers of amino acids represented by such abbreviations are in L-configuration unless otherwise specified.

| | |
|---|---|
| DNA: | deoxyribonucleic acid |
| RNA: | ribonucleic acid |
| A: | adenine |
| T: | thiamine |
| G: | guanine |
| C: | cysteine |
| dNTP: | deoxynucleotide triphosphate |
| ddNTP: | dideoxynucleotide triphosphate |
| dCTP: | deoxycytidine triphosphate |
| SDS: | sodium dodecyl sulphate |
| Ala: | alanine |
| Arg: | arginine |
| Asn: | asparagine |
| Asp: | aspartic acid |
| Cys: | cysteine |
| Gln: | glutamine |
| Glu: | glutamic acid |
| Gly: | glycine |
| His: | histidine |
| Ile: | isoleucine |
| Leu: | leucine |
| Lys: | lysine |
| Met: | methionine |
| Phe: | phenylalanine |
| Pro: | proline |
| Ser: | serine |
| Thr: | threonine |
| Trp: | tryptophane |
| Tyr: | tyrosine |
| Val: | valine |

"d.s.b." and "DE" are the abbreviations of dry solid basis and dextrose equivalent.

DESCRIPTION OF THE PRIOR ART

As described, for example, in U.S. Pat. No. 3,654,082, *Archives of Biochemistry and Biophysics*, Vol. 145, pp. 105–114 (1971), *Biochimica et Biophysica Acta*, Vol. 566, pp. 88–99 (1979), *Agricultural and Biological Chemistry*, Vol. 46, No. 3, pp. 639–646 (1982), and ibid., Vol. 47, No. 8, pp. 1761–1768 (1983), it has been known that an enzyme which forms maltotetraose from starch, or maltotetraose-forming amylase (EC 3.2.1.60) is produced by a microorganism of the species *Pseudomonas stutzeri*.

These prior arts only teach a part of its enzymatic properties, and such teaching is not enough to use maltotetraose-forming amylase in a supply which is sufficiently stable and safe for industrial applications. Thus, an improved process for obtaining maltotetraose-forming amylase has been in great demand.

SUMMARY OF THE INVENTION

The present inventors studied such maltotetraose-forming amylase, specifically, a polypeptide possessing maltotetraose-forming amylase activity with a revealed amino acid sequence, and its uses. The polypeptide possessing maltotetraose-forming amylase activity will hereinafter be referred to as "polypeptide".

As a result, the present inventors found that such polypeptide comprises one or more partial amino acid sequences selected from the group consisting of (a) Asp-Val-Val-Pro-Asn-His-Met, (b) Arg-Phe-Asp-Phe-Val-Arg-Gly-Tyr, (c) Phe-Cys-Val-Gly-Glu-Leu-Trp-Lys-Gly, and (d) Thr-Phe-Val-Asp-Asn-His-Asp-Thr, and, more particularly, that these partial amino acid sequences are located in this order with respect to the N-terminal of the polypeptide.

Polypeptide has features that it acts on starch to mainly produce maltotetraose, and that it has a molecular weight of $50,000 \pm 10,000$ when electrophoresed on SDS-polyacrylamide gel.

BRIEF DESCRIPTION OF THE ACCOMPANYING DRAWINGS

DETAILED DESCRIPTION OF THE INVENTION

In the present invention, the amino acid sequence of polypeptide was determined first by cloning a polypeptide gene in a maltotetraose-forming amylase producing microorganism, then decoding the polypeptide gene.

The amino acid sequence containing N-terminal was determined by purifying polypeptide substantially to homogeneity, and subjecting it to a gas-phase protein sequencer.

Cloning of Polypeptide Gene

A DNA component is isolated from a donor microorganism capable of producing polypeptide, purified and spliced, for example, with ultrasonic or restriction enzymes to obtain a DNA fragment. The obtained DNA fragment and a vector fragment, obtained by cleaving a vector in the same manner, are ligated, for example, with a DNA ligase to obtain a recombinant DNA carrying polypeptide gene.

The donor microorganism is chosen from polypeptide producing microorganisms. Examples of such microorganisms are *Pseudomonas stutzeri* NRRL B-3389 described in U.S. Pat. No. 3,654,082; *Pseudomonas stutzeri* MO-19 newly isolated from a soil sample by the present inventors; their mutants; and transformed microorganisms in which polypeptide producibility has been introduced by genetic engineering technique.

*Pseudomonas stutzeri* MO-19 was found and isolated from a soil sample in Kayo-cho, Jobo-gun, Okayama, Japan. A deposit of the microorganism was made on Feb. 13, 1987 at the Fermentation Research Institute, Agency of Industrial Science and Technology, Ministry of International Trade and Industry, 1–3, Higashi, 1-chome, Tsukuba-shi, Ibaraki-ken, 305, Japan, and has been allocated the Deposit Number FERM BP-1682.

The following is the taxonomy of *Pseudomonas stutzeri* MO-19.

Figure 1:
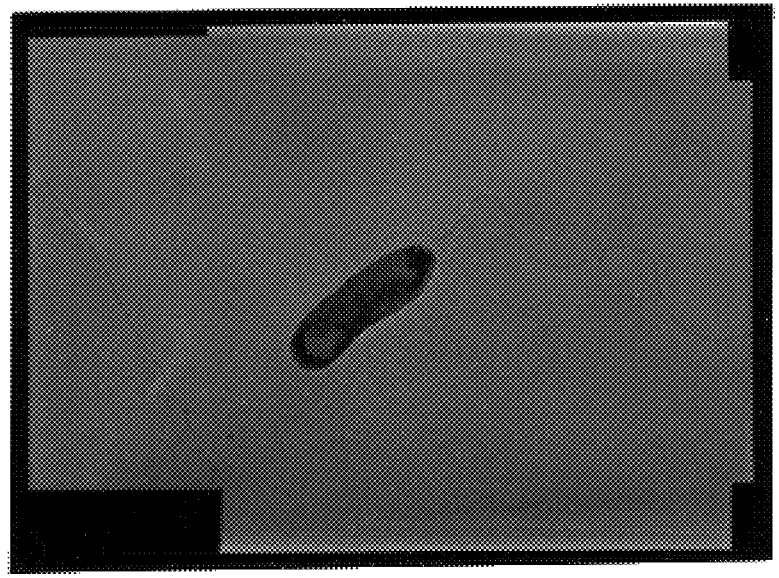
FIG. 1 shows an electron microscopic figure (×10,000) illustrating the cell form of *Pseudomonas stutzeri* FERM BP-1682.

A. Cell morphology:
  (a) Cell form and size
    Rod-shaped, 0.5–0.6×1.0–1.2 micrometers
    FIG. 1 of the accompanying drawings shows an electron microscopic figure (×10,000) of the cells of *Pseudomonas stutzeri* MO-19.
  (b) Cell polymorphism
    Unpresent
  (c) Motility
    Motile
  (d) Flagellum conditions
    Polar monotrichous
  (e) Spore and sporangium
    Not forming
  (f) Gram reaction
    Negative
  (g) Acid-fast
    Negative.

B. Cultivation Properties:
  (a) Cultivation on meat broth agar plate (28° C., 2 days)
    Cell growth is relatively fast and its colony is 1–3 mm in diameter. The colony has an opaque, glistening and brownish yellow oval form, as well as having a smooth surface.
  (b) Cultivation on meat broth agar slant (28° C., 2 days)
    Cell growth is moderate. Colony has an opaque, glistening and brownish yellow feather-like form, as well as having a plane rise. Does not produce soluble pigment.
  (c) Cultivation in a meat broth liquid culture medium (28° C., 2 days)
    After one-day cultivation, the microorganism renders the culture medium slight turbidity, and, after 2-day cultivation, the culture medium becomes strongly turbid. Cell grows relatively fast forming a membrane-like substance on the surface of the liquid culture medium, and gas or pigment is not formed.
  (d) Meat broth stab culture (28° C., 2 days) Growing in chain-like form around the stabbed area
  (e) Meat broth gelatin stab culture
    Does not liquefy gelatin
  (f) Litmus and milk (28° C., 5 days)
    The culture medium becomes alkaline within 5-day cultivation, and solidification of the milk is observed.

C. Physiological properties:
  (a) Reduction of nitrate
    Positive
  (b) Denitrification reaction
    Positive
  (c) M-R reaction
    Negative
  (d) V-R test
    Negative
  (e) Production of indol
    Negative
  (f) Production of $H_2S$
    Positive
  (g) Hydrolysis of starch
    Hydrolyzed
  (h) Utilization of citrates
    Positive
  (i) Utilization of inorganic nitrogen
    Ammonium salts and nitrates are both utilized
  (j) Production of pigment
    Does not produce soluble pigment
  (k) Oxidase
    Positive
  (l) Catalase
    Positive
  (m) Temperature- and pH-ranges for cell growth
    Cell grows relatively fast in a pH range of 4–7, but does not grow at pH 2 or lower, or pH 8 or higher. Cell grows relatively fast at a temperature in the range of 16–35° C., but does not grow at a temperature of 2° C. or lower, or 42° C. or higher.
  (n) Cell growth in the presence of oxygen
    Aerobic
  (o) O-F test
    Oxidative
  (p) Acid and gas formation from saccharide
    Acid is formed from D-glucose, D-mannose, lactose, maltose and starch, but not formed from L-arabinose, D-xylose, D-fructose, sucrose and glycerol. Gas is formed from D-mannose but not formed from the other saccharides.
  (q) Growth pH
    pH 7.7 (proteose peptone glucose medium)
  (r) Hydrolysis of cellulose
    Negative.

Based on the above described taxonomy and with reference to *Bergey's Manual of Determinative Bacteriology*, 7th edition (1957) and 8th edition (1974), the microorganism was identified as a microorganism of the species *Pseudomonas stutzeri* and named *Pseudomonas stutzeri* MO-19.

A discovered DNA can be prepared by culturing a donor microorganism, for example, with a liquid culture medium for about 1–3 days under agitation-aeration conditions, centrifugally separating the cells from the culture, and lysing the cells with a conventional procedure. Examples of such procedures are cytohydrolytic enzyme treatment, for example, lysozyme or β-glucanase, and ultrasonic treatment. Other enzyme such as protease, surface-active agent such as sodium lauryl sulfate and/or freezing-thawing treatment can be freely used in combination, if necessary.

In order to isolate and purify DNA from the resultant lysate, two or more conventional procedures such as phenol extraction, protein removal, protease treatment, ribonuclease treatment, alcohol sedimentation, and centrifugation can be used in combination.

Although cleavage of DNA can be effected, for example, by ultrasonic treatment or restriction enzymes treatment. The use of restriction enzymes, in particular, Type II restriction enzymes, for example, Sau3AI, EcoRI, HindIII, BamHI, SalI, SlaI, XmaI, XbaI, SacI, PstI, etc., that act on a specific nucleotide sequence, can facilitate smooth ligation of the cleaved DNA- and vector-fragments.

Bacteriophages and plasmids which autonomically proliferate in a host microorganism are suitable for a vector.

When a microorganism of the species *Escherichia coli* is used as the host, bacteriophages such as $\lambda gt:\lambda C$ and $\lambda gt.\lambda B$ are employable, while ρ11, ψ1 and ψ105 are usable when a microorganism of the species *Bacillus subtilis* is used as the host.

As regards plasmids, when a microorganism of the species *Escherichia coli* is used as the host, plasmids such as pBR322 and pBR325 are employable, while pUB110, pTZ4 (pTP4) and pC194 are usable for a host microorganism of the species *Bacillus subtilis*. Plasmids, for example, pHV14, TRp7, YEp7 and pBS7, which autonomically proliferate in two or more different host microorganisms such as *Escherichia coli* and *Bacillus subtilis*, can be used as a vector. These vectors are cleaved with a restriction enzyme similarly as in cleavage of DNA to obtain a vector fragment.

DNA- and vector-fragments are ligated with conventional procedure using a DNA ligase. For example, DNA- and vector-fragments are first annealed, then subjected in vitro to the action of a suitable DNA ligase to obtain a recombinant DNA. If necessary, such recombinant DNA can be prepared by introducing the annealed fragments into a host microorganism, and subjecting the annealed fragments in vivo to a DNA ligase.

The host microorganisms usable in the invention are those in which the recombinant DNA autonomically and consistently proliferates to express its characteristics. Specifically, microorganisms which are not capable of producing α-amylase (EC 3.2.1.1) can be advantageously used because the use of such microorganisms facilitates determination, isolation and purification of a secreted polypeptide.

The recombinant DNA can be introduced into a host microorganism with a conventional procedure. For example, when a host microorganism belongs to the species *Escherichia coli*, introduction of recombinant DNA is effected in the presence of calcium ion, while the competent cell- and protoplast-methods are employable when a host microorganism of the genus Bacillus is used.

A transformed microorganism in which a recombinant DNA has been introduced is selected by collecting clone(s) which grows on a plate culture containing starch to convert the starch into maltotetraose.

The present inventors found that the recombinant DNA carrying polypeptide gene cloned in this way can be easily recovered from the transformed microorganism, and introduced into another host microorganism. Also it was found that the recombinant DNA fragment carrying polypeptide gene is then easily ligated with a vector fragment which can be obtained by splicing a vector such as plasmid in the same manner.

Furthermore, the present inventors found that the polypeptide gene in the recombinant DNA loses its ability to express characteristics when subjected to SmaI, a restriction enzyme commercialized by Toyobo Co., Ltd., Osaka, Japan.

Sequence of Polypeptide Gene

Polypeptide gene is decoded by the chain-terminator method described in *Gene*, Vol. 9, pp. 259–268 (1982).

In this method, a DNA fragment carrying a cloned polypeptide gene is inserted into a cloning site of a plasmid such as pUC18 with a restriction enzyme. The obtained recombinant plasmid is introduced by transformation into a suitable strain of the species *Escherichia coli* such as *Escherichia coli* JM83, followed by selection of a microorganism containing the recombinant plasmid.

Such microorganism is proliferated and then used to prepare a recombinant plasmid.

The obtained recombinant plasmid is annealed together with a synthetic primer, and Klenow fragment is then allowed to act on the annealed product to extend the primer. Thus, a complementary DNA is obtained.

Thereafter, the reaction mixture is subjected sequentially to polyacrylamide gel electrophoresis and radio-autography, followed by determination of polypeptide gene.

A sequence of a signal peptide which triggers off intracellular secretion of polypeptide can be determined in the same manner.

Amino Acid Sequence of Polypeptide

An amino acid sequence of polypeptide is determined with a DNA sequence of polypeptide gene.

An amino acid sequence of a signal peptide which triggers off intracellular secretion of polypeptide can be determined in the same manner.

Partial Amino Acid Sequence Containing N-terminal of Polypeptide

A polypeptide producing microorganism of the species *Pseudomonas stutzeri* is cultured with a nutrient culture medium to produce a polypeptide. After completion of the culture, the supernatant, centrifugally separated from the culture, is purified by ammonium sulfate fractionation, ion exchange chromatography and high-performance liquid chromatography to obtain a high-purity polypeptide specimen. The specimen is then degraded with a gas-phase protein sequencer in accordance with the method described in *Journal of Biological Chemistry*, Vol. 256, pp. 7990–7997 (1981), with high-performance liquid chromatography, and determined for its identified partial amino acid sequence containing N-terminal.

Preparation of Polypeptide with Transformed Microorganism

The present inventors found that a large amount of polypeptide can be consistently produced by culturing a transformed microorganism with a nutrient culture medium.

Into the nutrient culture medium is incorporated, for example, carbon source, nitrogen source, minerals, and, if necessary, a small amount of organic nutrient such as amino acid and vitamin.

Starch, partial starch hydrolysate, and saccharides such as glucose, fructose and sucrose are suitable for the carbon sources. Inorganic nitrogen sources such as ammonia gas, ammonia water, ammonium salts and nitrates; and organic nitrogen sources such as peptone, yeast extract, defatted soy-bean, corn steep liquor and meat extract are suitable for the nitrogen sources.

Cultivation of a transformed microorganism is carried out with a nutrient culture medium for about 1–4 days under aerobic conditions such as agitation-aeration conditions to accumulate polypeptide while keeping the nutrient culture medium, for example, at pH 4–10 and 25–65° C.

Although the polypeptide in the resultant culture may be used intact, generally, the culture is separated into a polypeptide solution and a cell with a conventional procedure such as filtration and centrifugation, prior to its use.

A polypeptide present in a cell is first treated with ultrasonic, surface-active agent and/or cytohydrolytic enzyme, then with filtration and centrifugation to obtain a polypeptide solution.

The polypeptide solution is purified by appropriately combining, for example, with concentration in vacuo, concentration using membrane filter, adsorption/elution using starch, salting-out using ammonium sulfate or sodium sulfate, and fractional sedimentation using methanol, ethanol or acetone into a much more homogenous form, prior to its use. The obtained polypeptide can be advantageously used when immobilized with a conventional method such as carrier-linkage, cross-linkage and entrapment.

Polypeptide usable in the present invention should not be restricted to one derived from the above described transformed microorganism, as long as it has been elucidated that the polypeptide has a specified amino acid sequence and can be safely used.

In an industrial-scale preparation of high maltotetraose using the polypeptide according to the present invention, desirably, an amylaceous substance, for example, starch, amylopectin, amylose and partial starch hydrolysate is used as substrate. In preparation of food products containing amylaceous substances, the food products can be subjected to the action of the polypeptide to form maltotetraose therein in order to prevent possible retrogradation of the amylaceous substances and prolong their shelf-lives, if necessary.

Usually, a solution containing about 5–45 w/w % amylaceous substance is added with the polypeptide in an amount of about 1–20 units/g amylaceous substance, and the enzymatic reaction is continued for 0.5–3 days at pH 5–9 and about 40–70° C.

In this case, the presence of about 0.0005–0.05 mole calcium salt such as calcium chloride in the reaction solution improves the thermostability of the polypeptide, as well as facilitating its enzymatic reaction.

In order to increase the maltotetraose content in the reaction mixture to the possible highest level, desirably, an amylaceous substance having the possible lowest degree of liquefaction by acid or α-amylase, in other words, DE of 15 or lower, preferably, lower than 6, is subjected to the action of the polypeptide.

The composition and content of the obtained high maltotetraose can be freely changed and increased to meet its final use by using the polypeptide in combination with starch-degrading enzymes, for example, cyclomaltodextrin glucanotransferase (EC 2.4.1.19), α-amylase (EC 3.2.1.1), β-amylase (EC 3.2.1.2), glucoamylase (EC 3.2.1.3), α-glucosidase (EC 3.2.1.20), pullulanase (EC 3.2.1.41) and isoamylase (EC 3.2.1.68).

More particularly, polypeptide can be advantageously used together with one or more starch debranching enzymes, for example, pullulanase and isoamylase, in order to increase the content of a high maltotetraose to 60–80 w/w %, d.s.b.

The content of a high maltotetraose having about 40–80 w/w %, d.s.b. can be freely increased by removing contaminating saccharides and dextrins therefrom with a suitable method such as fractionation.

Examples of such fractionation include that using semipermeable membranes as disclosed in Japanese Patent Laid-Open No. 4647/73, that using organic precipitants as disclosed in Japanese Patent Laid-Open No. 102854/74, and that using strongly-acidic cation exchange resins as disclosed in Japanese Patent Laid-Open No. 148794/84. A high maltotetraose having the possible highest purity not lower than 98 w/w % can be easily obtained by employing the fractionation, if necessary.

Thereafter, the obtained high maltotetraose is usually filtered, purified with decoloration using activated charcoal and deionization using ion exchange resins in H- and OH-form, and concentrated into syrup which can be freely dried into powder, if necessary.

The high maltotetraose thus obtained contains 40 w/w % or more maltotetraose, d.s.b.

High maltotetraose can be advantageously reduced into a chemically stabler high maltotetraitol.

For example, an about 40–60% aqueous solution of high maltotetraose is placed in an autoclave, and added with about 8–10% Raney Nickel as the catalyst. The mixture is heated to 90–140° C. while stirring, and hydrogenated at this temperature under a hydrogen pressure of 20–150 kg/cm$^2$. After completion of the hydrogenation, the Raney Nickel is removed from the reaction mixture, and the residue is purified with activated charcoal and ion exchange resins similarly as in the preparation of high maltotetraose. The resultant may be concentrated into syrup or dried into powder.

The obtained high maltotetraitol usually contains 40 w/w % or more maltotetraitol, d.s.b.

High maltotetraose and high maltotetraitol, obtained by the above described methods, can be extensively used in food products as a sweetener with a moderate sweetness, as well as a body-imparting agent, viscosity-controlling agent, humectant, gloss-imparting agent, adhesive, flavor-retaining agent, crystallization-preventing agent, sticking-preventing agent for candy, retrogradation-preventing agent, and nutrient supplement.

For example, coating of food products with a heated syrup of high maltotetraose or high maltotetraitol has the features that it hardens and dries faster the food products and causes less sticking than in the case of using conventional saccharides, as well as that it imparts excellent gloss and texture to the food products.

High maltotetraose and high maltotetraitol can be used alone, or, if necessary, in combination with one or more sweeteners, for example, glucose, maltose, isomerized sugar, sugar, honey, maple sugar, sorbitol, maltitol, paratinose, dihydrochalcone, stevioside, α-glycosyl stevioside, sweet substance derived from *Momordica grosvenori* Swingle, glycyrrhizin, α-glycosyl glycyrrhizin, L-asparatyl-L-phenylalanine methyl ester, saccharin, glycine and alanine.

Since high maltotetraose and high maltotetraitol well harmonize with substances effecting acidity-, salty-, astringent-, delicious- or bitter-taste and exert a high thermal resistance, they can be favorably used in food products in order to sweeten and/or season them, as well as to improve their taste quality.

High maltotetraose and high maltotetraitol can be freely used in seasonings, for example, soy sause, powdered soy sause, "miso (a kind of Japanese seasoning prepared by fermenting rice, wheat, barley and beans)", "funmatsu-miso (powdered miso)", "moromi (an unrefined sake)", "hishio (a salted meat)", "furikake (a seasoned fish meal)", mayonnaise, dressing, vinegar, "sanbai-zu (a mixture seasoning comprising soy sauce, vinegar, sake and sugar)", "funmatsu-sushi-no-moto (a premix for seasoning sushi)", "chuka-no-moto (an instant mix of Chinese dish)", "tent-suyu (a sauce for Japanese deep-fat fried food)", "mentsuyu (a sauce for Japanese vermicelli)", sauces, catsup, "yakiniku-no-tare (a sauce for Japanese grilled meat)", curry roux, instant stew mix, instant soup mix, "dashino-moto (an instant stock mix)", mixed seasoning, "mirin (a sweet sake)", "shin-mirin (a synthetic mirin)", table syrup and coffee sugar.

High maltotetraose and high maltotetraitol can be freely used to sweeten food products, for example, "wagashi (Japanese-style confectioneries)" such as "senbei (rice crackers)", "arare-mochi (pellet-shaped senbei)", "okoshi (a millet-and-rice cake)", rice paste, "manju (a bun with a bean-jam filling)", "uiro (a sweet rice jelly)", "an (a bean jam)", "yokan (a sweet jelly of beans)", "mizu-yokan (a soft adzuki-bean jelly)", "kingyoku (a kind of yokan)", jelly, "pao de Castella (a sponge cake)" and "amedama (toffees)"; confectioneries and bakery products such as bun, biscuit, cracker, cookie, pie, pudding, butter cream, custard cream, cream puff, waffle, sponge cake, doughnut, chocolate, chewing gum, caramel and candy; frozen desserts such as ice cream and shurbet; syrups such as "kajitsu-no-syrup-zuke (a preserved fruit)" and "kori-mitsu (a sugar syrup for shaved ice)"; processed grains such as noodles, rices and artificial meats; pastes such as flour paste, peanut paste, fruit paste and spread; processed fruits and vegetables such as jam, marmalade, "syrup-zuke (fruit pickles)", and "toka (conserves)"; pickles and pickled products such as "fukujin-zuke (red colored radish pickles)", "bettara-zuke (a kind of whole fresh radish pickles)", "senmai-zuke (a kind of sliced fresh radish pickles)" and "rakkyo-zuke (pickled shallots)", premixes for pickles and pickled products such as "takuan-zukeno-moto (a premix for pickled radish)" and "hakusai-zuke-no-moto (a premix for fresh white rape pickles)"; meat products such as ham and sausage; fish meat products such as fish ham, fish sausage, "kamaboko (a steamed fish paste)", "chikuwa (literally bamboo wheels)", and "tenpura (a Japanese deep-fat fried fish paste)"; "chinmi (relish)" such as "uni-no-shiokara (salted guts of sea urchin)", "ikura-no-shiokara (salted guts of squid)", "su-konbu (a processed tangle)", "saki-surume (dried squid strips)" and "fugu-no-mirinboshi (a dried mirin-seasoned swellfish)"; "tsukudani (foods boiled down in soy)", such as those of layer, edible wild plants, dried squid, fish and shellfish; daily dishes such as "nimane (cooked beans)", potato salad and "konbu-maki (a tangled roll)"; dairy products such as processed cheese and milk powder; canned and bottled products such as those of meat, fish meat, fruit and vegetable; alcoholic beverages such as synthetic sake, fruit wine and liquors; soft drinks such as coffee, cocoa, juice, carbonated beverage, sour milk beverage and beverage containing a lactic bacterium; and instant food products such as instant pudding mix, instant hot cake mix, juice powder, instant coffee, "sokuseki-shiruko (an instant mix of adzuki-bean soup with rice cake)" and instant soup mix, as well as to improve their taste quality and physical properties.

High maltotetraose and high maltotetraitol, more particularly, high maltotetraose with an excellent assimilability can be advantageously used in nutrient supplements, for example, those for hemodialysis or fluid foods for intubation feeding or baby foods for sick persons, convalescent feeble persons, the aged or infants who can not take normal food products.

In this case, one can prepare a liquid nutrient supplement, which can be used without further processings, as well as preparing a solid nutrient supplement, for example, those in powder and granules, which is dissolved, for example, in water, salt solution, fruit juice and milk, prior to its use.

High maltotetraose and high maltotetraitol can be used in feeds and pet foods for domestic animal and fowl, honey bee, silkworm and fish in order to improve their taste quality.

In addition, high maltotetraose and high maltotetraitol can be used to sweeten tobaccos, cosmetics, toiletries and pharmaceuticals in solid, paste or liquid form, such as cigar, cigarette, dentrifrice, lipstick, lipcream, medicine for internal administration, troche, liver oil drop, oral refreshment agent, cachou and collutrium, as well as to improve their taste quality.

As described above, the wording "food products" as referred to in the present invention shall mean all products that can be orally taken as well as meaning nutrient supplements such as fluid foods for intubation feeding.

To incorporate high maltotetraose or high maltotetraitol into food products, any conventional method can be employed so far as high maltotetraose or high maltotetraitol can be incorporated into the food products, before completion of their processings, for example, with kneading, mixing, dissolving, melting, dipping, impregnating, applying, coating, spraying and injecting.

Detailed description of the present invention will hereinafter be explained by the following Experiments.

Experiment 1

Cloning of *Pseudomonas stutzeri* Polypeptide Gene into *Escherichia coli*

Experiment 1-(1)

Preparation of Chromosome DNA Carrying Polypeptide Gene of *Pseudomonas stutzeri*

A chromosome DNA carrying a polypeptide gene of a microorganism of the species *Pseudomonas stutzeri* was prepared in accordance with the method described by Saito and Miura, in *Biochimica et Biophisica Acta*, Vol. 72, pp. 619–629 (1963). A seed culture of *Pseudomonas stutzeri* MO-19 was cultured with brain heart infusion medium at 30° C. overnight under agitation-aeration conditions. A cell, centrifugally separated from the culture, was suspended with TES buffer (pH 8.0) containing Tris-aminomethane, hydrochloric acid, EDTA and sodium chloride, added with 2 mg/ml of lysozyme, and incubated at 37° C. for 30 minutes. The incubated mixture was frozen allowed to stand at −20° C. overnight, added with TSS buffer (pH 9.0) containing Tris-aminomethane, hydrochloric acid, sodium lauryl sulfate and sodium chloride, heated to 60° C., added with a mixture of TES buffer (pH 7.5) and phenol (1:4 by volume), cooled in ice-chilled water, and centrifuged to obtain a supernatant. To the supernatant was added two volumes of cold ethanol to recover a crude chromosome DNA which was then dissolved in SSC buffer (pH 7.1) containing sodium chloride and trisodium citrate, thereafter, the mixture was subjected to both "RNase A", a ribonuclease commercialized by Sigma Chemical Co., Missouri, USA, and "Pronase E", a protease commercialized by Kaken Pharmaceutical Co., Ltd., Tokyo, Japan, added with a fresh preparation of TES buffer and phenol mixture, cooled and centrifuged to obtain a supernatant. The supernatant was added with two volumes of cold ethanol to recover a purified chromosome DNA. The chromosome DNA was dissolved in a buffer (pH 7.5) containing Tris-aminomethane, hydrochloric acid and EDTA, and stored at −20° C.

Experiment 1-(2)

Preparation of Plasmid pBR322

Plasmid pBR322 (ATCC 37017) was isolated from a microorganism of the species *Escherichia coli* in accordance with the method described by J. Meyers et al. in *Journal of Bacteriology*, Vol. 127, pp. 1524–1537 (1976).

Experiment 1-(3)

Preparation of Recombinant DNA Carrying Polypeptide Gene

The purified chromosome DNA carrying polypeptide gene, prepared in Experiment 1-(1), was partially digested with Sau3AI, a restriction enzyme commercialized by Nippon Gene Co., Ltd., Toyama, Japan, to give a DNA fragment of 1–20 kbp. Separately, the pBR322 specimen, prepared in Experiment 1-(2), was completely cleaved with BamHI, a restriction enzyme commercialized by Nippon Gene Co., Ltd. to obtain a plasmid fragment. The plasmid fragment was subjected to *Escherichia coli* alkali phosphatase, commercialized by Takara Shuzo Co., Ltd., Kyoto, Japan, to prevent self-ligation of the plasmid fragment, as well as to dephosphorize the 5'-terminal of the fragment.

Both ends of the resultant plasmid fragment were then ligated by subjecting them to $T_4$ DNA ligase, commercialized by Nippon Gene Co., Ltd., at 4° C. overnight to obtain a recombinant DNA.

Experiment 1-(4)
Introduction of Recombinant DNA into *Escherichia coli*

*Escherichia coli* HB101 (ATCC 33694), a microorganism incapable of producing amylase, was used as a host.

The microorganism was cultured with L-broth at 37° C. for 4 hours, and a cell, centrifugally separated from the culture, was suspended with 10 mM acetate buffer (pH 5.6) containing 10 mM sodium chloride, 50 mM manganese chloride, centrifugally separated again, resuspended with 10 mM acetate buffer (pH 5.6) containing 25 mM calcium chloride and 125 mM manganese chloride, added with the recombinant DNA prepared in Experiment 1-(3), and allowed to stand in an ice-chilled water bath for 30 minutes. The mixture was then warmed to 37° C., added with L-broth, incubated at 37° C. for 30 minutes, spread on a L-broth agar plate medium containing 50 μg/ml of ampicillin and 2 mg/ml starch, and cultured at 37° C. for 24 hours to form colonies.

A colony which had degraded the starch into maltotetraose was selected by the iodine-coloration method. Thus, a transformed microorganism in which a recombinant DNA carrying polypeptide gene had been introduced was selected. The transformed microorganism was then proliferated, and the recombinant DNA was extracted from the proliferated microorganism by the plasmid preparation method in Experiment 1-(2), subjected to restriction enzymes to determine restriction cleavage sites, and partially digested with SalI, a restriction enzyme commercialized by Nippon Gene Co., Ltd. The digested product was subjected to $T_4$ DNA ligase similarly as in Experiment 1-(3) to obtain a recombinant DNA, followed by selection of a transformed microorganism in accordance with the method in Experiment 1-(4). The transformed microorganism contained a recombinant DNA of a relatively small-size that carried polypeptide gene.

One of these microorganisms and its recombinant DNA were named "*Escherichia coli* TPS618 (FERM BP-1681)" and "pTPS618" respectively.

Figure 2:
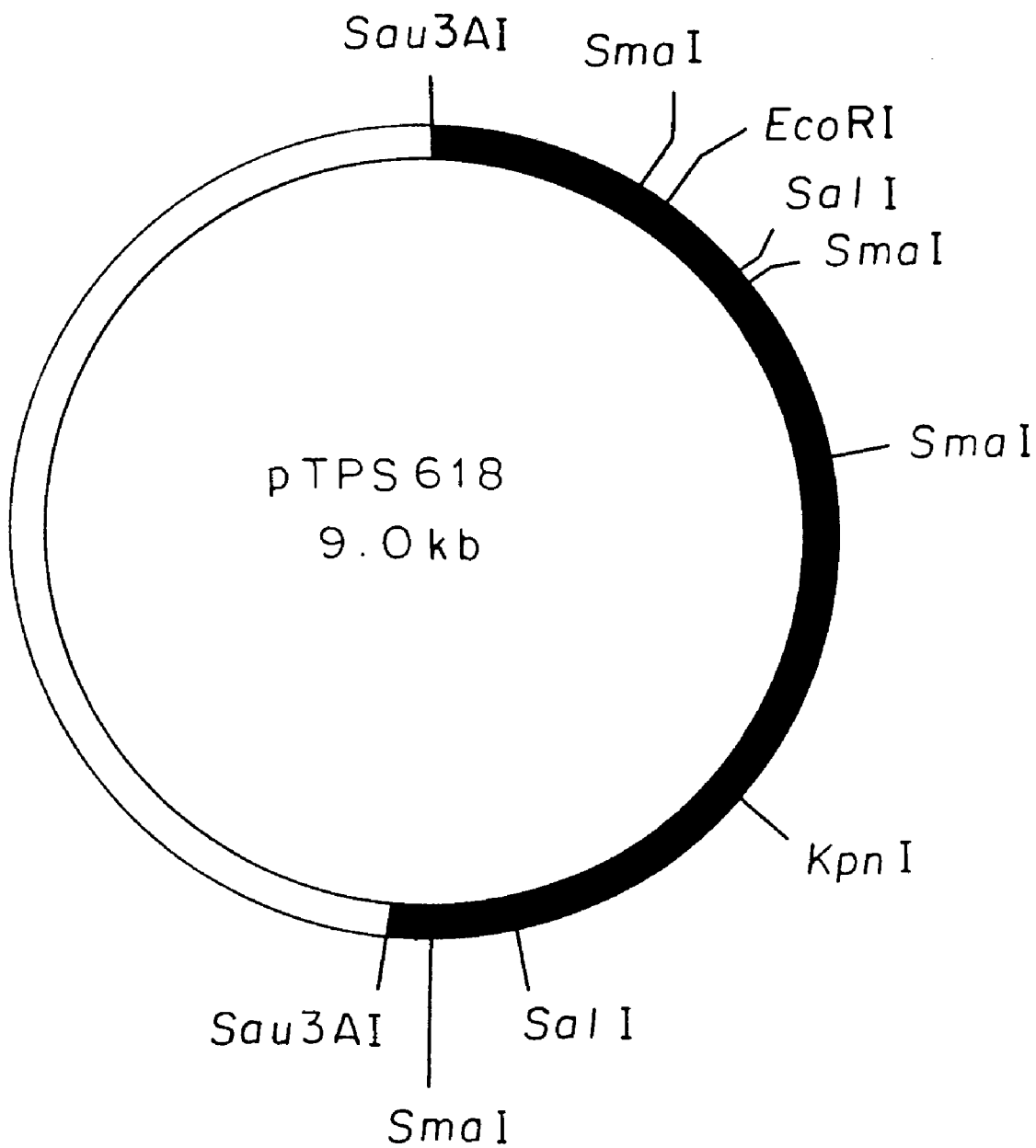
FIG. 2 shows a restriction map of recombinant DNA pTPS618 carrying polypeptide gene derived from a microorganism of the species *Pseudomonas stutzeri*.

The restriction map of recombinant DNA pTPS618, in particular, that of the DNA fragment derived from *Pseudomonas stutzeri* MO-19 is as shown in FIG. 2.

FIG. 2 clearly shows that this recombinant DNA is cleaved by either SmaI, a restriction enzyme commercialized by Toyobo Co., Ltd., EcoRI, SalI or KpnI, a restriction enzyme commercialized by Nippon Gene Co., Ltd., but not by BamHI, XhoI, BglII or XbaI, a restriction enzyme commercialized by Nippon Gene Co., Ltd.

Experiment 2
Partial Amino Acid Sequence Containing N-terminal of *Pseudomonas stutzeri* Polypeptide

Experiment 2-(1)
Preparation of Polypeptide

*Pseudomonas stutzeri* MO-19 was cultured with a liquid culture medium by the method in Experiment 4 to produce a polypeptide. A supernatant, centrifugally separated from the culture, was salted out with ammonium sulfate to obtain a polypeptide fraction. The polypeptide fraction was purified by column chromatography using "DEAE-Toyopearl 650S®", an anion exchange resin commercialized by Toyo Soda Manufacturing Co., Ltd., Tokyo, Japan, and "Mono Q®", an anion exchange resin commercialized by Pharmacia LKB Biotechnology Inc., Uppsala, Sweden, to obtain a high-purity polypeptide specimen.

On SDS-polyacrylamide electrophoresis in accordance with the method described by K. Weber and M. Osborn in *Journal of Biological Chemistry*, Vol. 244, page 4406 (1969), the polypeptide specimen showed a molecular weight of 50,000±10,000.

The specific activity of the polypeptide specimen was 600±150 units/mg protein.

One unit of the maltotetraose-forming amylase is defined as the amount of the enzyme that splits 1 micromole of glucosidic bonds per minute by the following procedure: Five milliliters of 1.0 w/v % soluble starch (pH 7.0) is added with 0.2 ml of an enzyme solution, and the mixture is incubated at 40° C. for 20 minutes to effect enzymatic reaction. Thereafter, the reaction mixture is added with the Somogyi's reagent to suspend the reaction. The resultant reducing sugar is measured by the Nelson-Somogyi method.

Experiment 2-(2)
Partial Amino Acid Sequence Containing N-terminal of Polypeptide A polypeptide specimen, prepared by the method in Experiment 2-(1), was fed to "Model 470A", a gas-phase protein sequencer commercialized by Applied Biosystems Inc., California, USA, and then analyzed with high-performance liquid chromatography to determine a partial amino acid sequence containing N-terminal of the polypeptide.

The partial amino acid sequence was Asp-Gln-Ala-Gly-Lys-Ser-Pro-Asn-Ala-Val-Arg-Tyr-His-Gly-Gly-Asp-Glu-Ile-Ile Leu.

Experiment 3
Sequence of Polypeptide Gene Derived from *Pseudomonas stutzeri* and Amino Acid Sequence of Polypeptide

Experiment 3-(1)
Preparation of Plasmid pUC18

Plasmid pUC18 was prepared in accordance with the method in Experiment 1-(2) from *Escherichia coli* JM83 (ATCC 35607) in which the plasmid had been introduced.

Experiment 3-(2)
Preparation of Recombinant DNA Carrying Polypeptide Gene

A recombinant DNA was prepared by the method in Experiment 1-(3).

A plasmid carrying polypeptide gene prepared by the method in Experiment 1-(2) was cleaved by restriction enzymes to prepare a fragment carrying polypeptide gene, and a plasmid pUC18 prepared by the method in Experiment 4-(1) was cleaved by restriction enzymes in the same manner to prepare a fragment. These fragments were subjected to $T_4$ DNA ligase to obtain a recombinant DNA.

Experiment 3-(3)
Introduction of Recombinant DNA into *Escherichia coli*

In this example, a microorganism of *Escherichia coli* JM83 was used as a host.

The recombinant DNA was introduced into this microorganism in accordance with the method in Experiment 1-(4) to transform the microorganism.

Transformed microorganisms were inoculated to a culture medium containing 5-bromo-4-chloro-3-indoyl-β-galactoside (Xgal) and cultured, followed by selection of a microorganism forming colorless plaque was selected.

Experiment 3-(4)
Preparation of Recombinant DNA from Transformed Microorganism A transformed microorganism was cultured on L-broth containing 50 μg/ml of ampicillin, and the obtained cell was then treated with the alkaline mini-preparation method to obtain a recombinant DNA.

Experiment 3-(5)
Sequence of Recombinant DNA

The recombinant DNA was decoded by the dideoxy chain terminator method.

The recombinant DNA, prepared in Experiment 3-(4), and a synthetic primer composed of 17 bases were mixed, annealed at 60° C. for 20 minutes, added with dNTP, ddNTP, ($\alpha$-$^{32}$P) dCTP and Klenow fragment, and reacted at 37° C. for 30 minutes to extend the primer towards the 3' site from the 5' site. Thus, a complementary DNA was obtained. To the complementary DNA was added an excessive amount of dNTP, and the mixture was reacted at 37° C. for 30 minutes, followed by addition of a formamide solution of dye mixture to suspend the reaction. The reaction mixture was boiled for 3 minutes, and electrophoresed on 6% polyacrylamide gel at about 25 mA to separate the extended complementary DNA. After completion of the electrophoresis, the gel was fixed and dehydrated.

The dehydrated gel was then autoradiographed, and the polypeptide gene was determined by analyzing base bands on the radioautogram.

The results were as shown in Table 1-1.

The signal peptide gene located upstream the 5'-terminal of the polypeptide gene was decoded in the same manner.

The results were as shown in Table 1-2.

Experiment 3-(6)
Amino Acid Sequence of Polypeptide

The amino acid sequence of polypeptide was determined with reference to the sequence as shown in Table 1-1, and the results were as shown in Table 2-1.

The amino acid sequence of the signal peptide was determined in the same manner, and the results were as shown in Table 2-2.

These evidences confirmed that the polypeptide derived from a microorganism of the species *Pseudomonas stutzeri* has the amino acid sequence as shown in Table 2-1.

TABLE 1-1

| 10 | 20 | 30 | 40 | 50 | 60 |
|---|---|---|---|---|---|
| GATCAGGCCG | GCAAGAGCCC | CAACGCTGTG | CGCTACCACG | GCGGCGACGA | AATCATTCTC |
| 70 | 80 | 90 | 100 | 110 | 120 |
| CAGGGCTTTC | ACTGGAACGT | CGTCCGCGAA | GCGCCCAACG | ACTGGTACAA | CATCCTGCGC |
| 130 | 140 | 150 | 160 | 170 | 180 |
| CAGCAGGCCG | CGACCATCGC | CGCCGACGGC | TTCTCGGCGA | TCTGGATGCC | GGTGCCCTGG |
| 190 | 200 | 210 | 220 | 230 | 240 |
| CGCGACTTCT | CCAGCTGGAG | CGACGGCAGC | AAGTCCGGCG | GCGGTGAAGG | CTACTTCTGG |
| 250 | 260 | 270 | 280 | 290 | 300 |
| CACGACTTCA | ACAAGAACGG | CCGCTATGGC | AGTGACGCCC | AGCTGCGTCA | GGCCGCCAGC |
| 310 | 320 | 330 | 340 | 350 | 360 |
| GCGCTCGGTG | GCGCCGGCGT | GAAAGTGCTT | TACGACGTGG | TGCCCAACCA | CATGAACCGT |
| 370 | 380 | 390 | 400 | 410 | 420 |
| GGCTATCCGG | ACAAGGAGAT | CAACCTCCCG | GCCGGCCAGG | GCTTCTGGCG | CAACGACTGC |
| 430 | 440 | 450 | 460 | 470 | 480 |
| GCCGACCCGG | GCAACTACCC | CAATGATTGC | GACGACGGCG | ACCGCTTCAT | CGGCGGCGAT |
| 490 | 500 | 510 | 520 | 530 | 540 |
| GCGGACCTCA | ACACCGGCCA | CCCGCAGGTC | TACGGCATGT | TCCGCGATGA | ATTCACCAAC |
| 550 | 560 | 570 | 580 | 590 | 600 |
| CTGCGCAGTC | AGTACGGTGC | CGGCGGCTTC | CGCTTCGACT | TTGTTCGGGG | CTATGCGCCG |
| 610 | 620 | 630 | 640 | 650 | 660 |
| GAGCGGGTCA | ACAGCTGGAT | GACCGATAGC | GCCGACAACA | GCTTCTGCGT | CGGCGAACTG |
| 670 | 680 | 690 | 700 | 710 | 720 |
| TGGAAAGGCC | CCTCTGAGTA | CCCGAACTGG | GACTGGCGCA | ACACCGCCAG | CTGGCAGCAG |
| 730 | 740 | 750 | 760 | 770 | 780 |
| ATCATCAAGG | ACTGGTCCGA | CCGGGCCAAG | TGCCCGGTGT | TCGACTTCGC | CCTCAAGGAA |
| 790 | 800 | 810 | 820 | 830 | 840 |
| CGCATGCAGA | ACGCTCGATC | GCCGACTGGA | AGCACGCCTG | AACGGCAATC | CCGACCCGCG |
| 850 | 860 | 870 | 880 | 890 | 900 |
| TGGCGCGAGG | TGGCGGTGAC | CTTCGTCGAC | AACCACGACA | CCGGCTACTC | GCCCGGGCAG |
| 910 | 920 | 930 | 940 | 950 | 960 |
| AACGGTGGGC | AGCACCACTG | GGCTCTGCAG | GACGGGCTGA | TCCGCCAGGC | CTACGCCTAC |
| 970 | 980 | 990 | 1000 | 1010 | 1020 |
| ATCCTCACCA | GCCCCGGTAC | GCCGGTGGTG | TACTGGTCGC | ACATGTACGA | CTGGGGTTAC |
| 1030 | 1040 | 1050 | 1060 | 1070 | 1080 |

TABLE 1-1-continued

```
GGCGACTTCA TCCGTCAGCT GATCCAGGTG CGTCGCGCCG CCGGCGTGCG CGCCGATTCG
         1090       1100       1110       1120       1130       1140
GCGATCAGCT TCCACAGCGG CTACAGCGGT CTGGTCGCCA CCGTCAGCGG CAGCCAGCAG
         1150       1160       1170       1180       1190       1200
ACCCTGGTGG TGGCGCTCAA CTCCGACCTG GGCAATCCCG GCCAGGTGGC CAGCGGCAGC
         1210       1220       1230       1240       1250       1260
TTCAGCGAGG CGGTCAACGC CAGCAACGGC CAGGTGCGCG TGTGGCGTAG CGGCACGGGC
         1270       1280       1290       1300       1310       1320
AGCGGTGGCG GTGAACCCGG CGCTCTGGTC AGTGTGACTT TCCGCTGCGA CAACGGCGCG
         1330       1340       1350       1360       1370       1380
ACGCAGATGG GCGACAGCGT CTACGCGGTC GGCAACGTCA GCCAGCTCGG TAACTGGAGC
         1390       1400       1410       1420       1430       1440
CCGGCCGCGG CGTTGCGCCT GACCGACACC AGCGGCTACC CGACCTGGAA GGGCAGCATT
         1450       1460       1470       1480       1490       1500
GCCTTGCCTG CCGGCCAGAA CGAGGAATGG AAATGCCTGA TCCGCAACGA GGCCAACGCC
         1510       1520       1530       1540       1550       1560
ACCCAGGTGC GGCAATGGCA GGGCGGGGCA AACAACAGCC TGACGCCGAG CGAGGGCGCC
         1570
ACCACCGTCG GCCGGCTC
```

TABLE 1-2

```
         10         20         30         40         50         60
ATGAGCCACA TCCTGCGAGC CGCCGTATTG GCGGCGATGC TGTTGCCGTT GCCGTCCATG
GCC
```

TABLE 2-1

```
         1   2   3   4   5   6   7   8   9   10  11  12  13  14  15
  1> Asp-Gln-Ala-Gly-Lys-Ser-Pro-Asn-Ala-Val-Arg-Tyr-His-Gly-Gly-
 16> Asp-Glu-Ile-Ile-Leu-Gln-Gly-Phe-His-Trp-Asn-Val-Val-Arg-Glu-
 31> Ala-Pro-Asn-Asp-Trp-Tyr-Asn-Ile-Leu-Arg-Gln-Gln-Ala-Ala-Thr-
 46> Ile-Ala-Ala-Asp-Gly-Phe-Ser-Ala-Ile-Trp-Met-Pro-Val-Pro-Trp-
 61> Arg-Asp-Phe-Ser-Ser-Trp-Ser-Asp-Gly-Ser-Lys-Ser-Gly-Gly-Gly-
 76> Glu-Gly-Tyr-Phe-Trp-His-Asp-Phe-Asn-Lys-Asn-Gly-Arg-Tyr-Gly-
 91> Ser-Asp-Ala-Gln-Leu-Arg-Gln-Ala-Ala-Ser-Ala-Leu-Gly-Gly-Ala-
106> Gly-Val-Lys-Val-Leu-Tyr-Asp-Val-Val-Pro-Asn-His-Met-Asn-Arg-
121> Gly-Tyr-Pro-Asp-Lys-Glu-Ile-Asn-Leu-Pro-Ala-Gly-Gln-Gly-Phe-
136> Trp-Arg-Asn-Asp-Cys-Ala-Asp-Pro-Gly-Asn-Tyr-Pro-Asn-Asp-Cys-
151> Asp-Asp-Gly-Asp-Arg-Phe-Ile-Gly-Gly-Asp-Ala-Asp-Leu-Asn-Thr-
166> Gly-His-Pro-Gln-Val-Tyr-Gly-Met-Phe-Arg-Asp-Glu-Phe-Thr-Asn-
181> Leu-Arg-Ser-Gln-Tyr-Gly-Ala-Gly-Gly-Phe-Arg-Phe-Asp-Phe-Val-
196> Arg-Gly-Tyr-Ala-Pro-Glu-Arg-Val-Asn-Ser-Trp-Met-Thr-Asp-Ser-
211> Ala-Asp-Asn-Ser-Phe-Cys-Val-Gly-Glu-Leu-Trp-Lys-Gly-Pro-Ser-
226> Glu-Tyr-Pro-Asn-Trp-Asp-Trp-Arg-Asn-Thr-Ala-Ser-Trp-Gln-Gln-
241> Ile-Ile-Lys-Asp-Trp-Ser-Asp-Arg-Ala-Lys-Cys-Pro-Val-Phe-Asp-
```

TABLE 2-1-continued

```
256> Phe-Ala-Leu-Lys-Glu-Arg-Met-Gln-Asn-Ala-Arg-Ser-Pro-Thr-Gly-
271> Ser-Thr-Pro-Glu-Arg-Gln-Ser-Arg-Pro-Ala-Trp-Arg-Glu-Val-Ala-
286> Val-Thr-Phe-Val-Asp-Asn-His-Asp-Thr-Gly-Tyr-Ser-Pro-Gly-Gln-
301> Asn-Gly-Gly-Gln-His-His-Trp-Ala-Leu-Gln-Asp-Gly-Leu-Ile-Arg-
316> Gln-Ala-Tyr-Ala-Tyr-Ile-Leu-Thr-Ser-Pro-Gly-Thr-Pro-Val-Val-
331> Tyr-Trp-Ser-His-Met-Tyr-Asp-Trp-Gly-Tyr-Gly-Asp-Phe-Ile-Arg-
346> Gln-Leu-Ile-Gln-Val-Arg-Arg-Ala-Ala-Gly-Val-Arg-Ala-Asp-Ser-
361> Ala-Ile-Ser-Phe-His-Ser-Gly-Tyr-Ser-Gly-Leu-Val-Ala-Thr-Val-
376> Ser-Gly-Ser-Gln-Gln-Thr-Leu-Val-Val-Ala-Leu-Asn-Ser-Asp-Leu-
391> Gly-Asn-Pro-Gly-Gln-Val-Ala-Ser-Gly-Ser-Phe-Ser-Glu-Ala-Val-
406> Asn-Ala-Ser-Asn-Gly-Gln-Val-Arg-Val-Trp-Arg-Ser-Gly-Thr-Gly-
421> Ser-Gly-Gly-Gly-Glu-Pro-Gly-Ala-Leu-Val-Ser-Val-Ser-Phe-Arg-
436> Cys-Asp-Asn-Gly-Ala-Thr-Gln-Met-Gly-Asp-Ser-Val-Tyr-Ala-Val-
451> Gly-Asn-Val-Ser-Gln-Leu-Gly-Asn-Trp-Ser-Pro-Ala-Ala-Ala-Leu-
466> Arg-Leu-Thr-Asp-Thr-Ser-Gly-Tyr-Pro-Thr-Trp-Lys-Gly-Ser-Ile-
481> Ala-Leu-Pro-Ala-Gly-Gln-Asn-Glu-Glu-Trp-Lys-Cys-Leu-Ile-Arg-
496> Asn-Glu-Ala-Asn-Ala-Thr-Gln-Val-Arg-Gln-Trp-Gln-Gly-Gly-Ala-
511> Asn-Asn-Ser-Leu-Thr-Pro-Ser-Glu-Gly-Ala-Thr-Thr-Val-Gly-Arg-
526> Leu
```

TABLE 2-2

```
Met-Ser-His-Ile-Leu-Arg-Ala-Ala-Val-Leu-Ala-Ala-Met-Leu-Leu-
Pro-Leu-Pro-Ser-Met-Ala
```

Experiment 4
Preparation of Polypeptide with Transformed Microorganism

Polypeptides were prepared with transformed microorganism of *Escherichia coli* TPS618, in which recombinant DNA carrying polypeptide gene derived from *Pseudomonas stutzeri* MO-19 had been introduced, and *Pseudomonas stutzeri* MO-19.

The polypeptide productivities of these transformed microorganism, host microorganism and *Pseudomonas stutzeri* MO-19 as the donor microorganism were compared in relation to their polypeptide activities.

A liquid culture medium containing 4 w/v % liquefied starch, 1.0 w/v % corn steep liquor, 0.5 w/v % polypeptone, 0.2 w/v % ammonium nitrate, 0.2 w/v % dipotassium hydrogen phosphate, 0.05 w/v % calcium chloride dihydrate, and water was adjusted to pH 7.2, sterilized by heating at 120° C. for 20 minutes, and cooled. In the case of *Escherichia coli* TPS618, it was inoculated to the liquid culture medium with 50 μg/ml of ampicillin, while that of *Escherichia coli* HB101, it was inoculated to the liquid culture medium without antibiotic. In each case, the microorganism was cultured at 37° C. for 24 hours under agitation-aeration conditions.

Separately, *Pseudomonas stutzeri* MO-19 was inoculated to the liquid culture medium without addition of antibiotic, and cultured at 28° C. for 24- and 96-hours. After centrifugal separation of each liquid culture medium into a supernatant and cell, the maltotetraose-forming amylase activity of the supernatant was assayed without further preparation. The cell was ultrasonically broken, prior to its assay, and its maltotetraose-forming amylase activity was determined based on the activity per volume of the liquid culture medium. The results were as shown in Table 3.

TABLE 3

| Microorganism | Maltotetraose-forming amylase activity (units/ml) | | | incubation period (hours) |
|---|---|---|---|---|
| | Supernatant | Cell | Total | |
| *Escherichia coli* TPS618 (FERM BP-1681) | 10 | 293 | 303 | 24 |
| *Escherichia coli* HB101 | 0 | 0 | 0 | 24 |
| *Pseudomonas stutzeri* MO-19 (FERM BP-1682) | 125 | 51 | 176 | 24 |

TABLE 3-continued

| Microorganism | Maltotetraose-forming amylase activity (units/ml) | | | incubation period (hours) |
|---|---|---|---|---|
| | Supernatant | Cell | Total | |
| Pseudomonas stutzeri MO-19 (FERM BP-1682) | 216 | 4 | 220 | 96 |

As evident from the results in Table 3, the transformed microorganism is advantageously usable in industrial-scale production of polypeptide because the transformed microorganism possesses an improved polypeptide productivity.

Supernatants obtained from these cultures were salted out with ammonium sulphate at a saturation degree of 0.4 to obtain crude polypeptide specimens. After study of these polypeptide specimens on their enzymatic properties such as saccharide transfer from starch to maltotetraose, optimum temperature, optimum pH, stable temperature and stable pH, these properties of the polypeptide specimens produced by the transformed microorganisms were in good accordance with those of the polypeptide at 24-hour culture of Pseudomonas stutzeri MO-19.

The polypeptide specimen at 96-hour culture of Pseudomonas stutzeri MO-19 differed in optimum temperature, optimum pH, stable temperature and stable pH from those of the polypeptide at 24-hour culture of Pseudomonas stutzeri MO-19, and was superior in acting on an amylaceous substance to the 24-hour culture of Pseudomonas stutzeri MO-19.

As described hereinafter, the polypeptide at 96-hour culture of Pseudomonas stutzeri MO-19 was highly purified, and studied in detail. The liquid culture medium was filtered with membrane filter, and the filtrate was salted out with ammonium sulphate to collect a fraction that precipitated at 0.2–0.4 saturation. The fraction was chromatographed on "DEAE-Toyopearl 650S®", an anion exchange resin commercialized by Toyo Soda Mfg. Co., Ltd., Tokyo, Japan, and "Mono Q®", an anion exchange resin commercialized by Pharmacia LKB Biotechnology Inc., Uppsala, Sweden, to obtain a solution containing a high-purity polypeptide which showed a single protein band on polyacrylamide gel electrophoresis.

This purification increased the specific activity of the polypeptide by about 4.3-folds, and the yield was about 48%.

The obtained maltotetraose-forming amylase with a specific activity of 680±60 units/mg protein has the following physicochemical properties:

(a) Action
Acting on starch to mainly produce maltotetraose
(b) Substrate specificity
Acting on starch, amylose, amylopectin, glycogen and β-limit dextrin; but substantially not acting on cyclodextrin, dextran, pullulan and elsinan.
(c) Optimum pH
About pH 7.0–7.5 at 40° C. for 20 minutes
(d) Stable pH
About pH 6.5–9.5 at 40° C. for 1 hour
(e) Optimum temperature
About 50° C. at pH 7.0 for 20 minutes
(f) Stable temperature
Up to about 45° C. at pH 7.0 for 1 hour. The activity is partially or completely retained at about 50° C. in the presence of $Ca^{2+}$, while at about 55° C. about 70% of the activity is retained.
(g) Inhibition and stabilization
Inhibited by $Hg^+$
Thermally stabilized by $Ca^{2+}$
(h) Molecular weight
46,000±1,000 on SDS-polyacrylamide gel electrophoresis
47,000±2,000 on ultracentrifugal analysis when calculated as (partial specific volume)×(density)=0.75
(i) Isoelectric point (pI)
About pI 4.8 on polyacrylamide gel isoelectric electrophoresis
(j) Ultraviolet absorption
About 275–280 nm.

Figure 3:
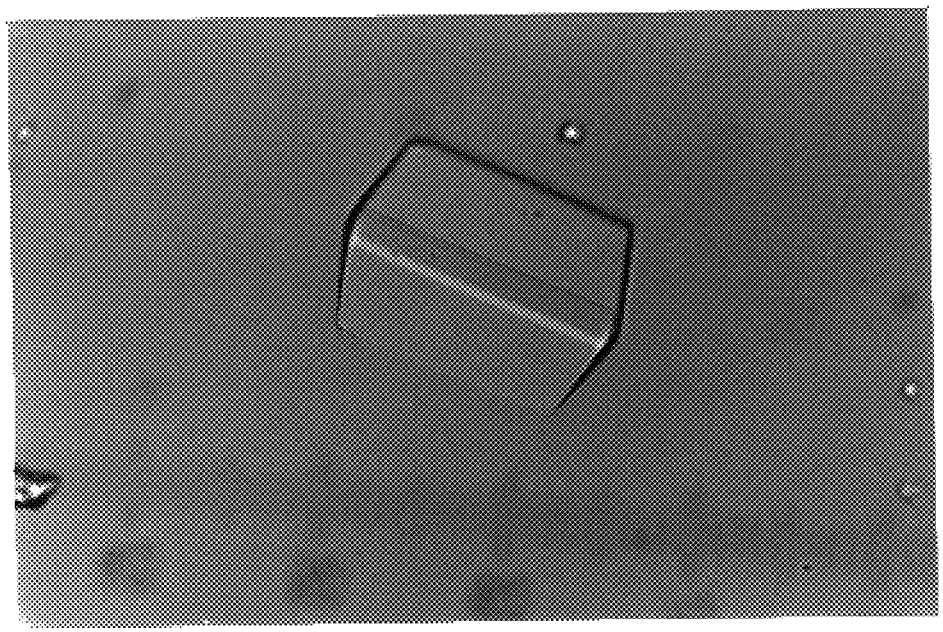
FIG. 3 shows a crystalline polypeptide when observed microscopically (×220).

One-month standing of about 1.0 w/v % high-purity polypeptide in 10 mM Tris-HCl buffer (pH 8.0) at 4° C. attained crystals. FIG. 3 is the microscopic figure (×220) of one of the crystals.

The high-purity polypeptide was subjected to the Edman degradation using a gas-phase protein sequencer, and the resultant degradation product was identified with high-performance liquid chromatography in accordance with the method described in The Journal of Biological Chemistry, Vol. 256, No. 15, pp. 7990–7997 (1981).

As a result, the sequence of 20 N-terminal amino acid residues of the polypeptide was Asp-Gln-Ala-Gly-Lys-Ser-Pro-Asn-Ala-Val-Arg-Tyr-His-Gly-Gly-Asp-Glu-Ile-Ile-Leu.

An amino acid sequence of the C-terminal of the polypeptide was determined in accordance with the method described in The Journal of Biological Chemistry, Vol, 248, No. 7, pp. 2296–2302 (1973).

As a result, Ala, Gly, Pro and Glu were located in this order with respect to the C-terminal of the polypeptide.

Based on the results obtained in these Experiments, it is determined that the polypeptide at 96-hour culture has the amino acid sequence as shown in Table 4.

By making a comparison between Tables 2-1 and 4, it is estimated that the C-terminal of the polypeptide as shown in Table 2-1, which has been produced at the early incubation period, is cleaved during the incubation period and converted into the polypeptide as shown in Table 4 with a lower molecular weight than that of the polypeptide as shown in Table 2-1.

TABLE 4

| | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1> | Asp | Gln | Ala | Gly | Lys | Ser | Pro | Asn | Ala | Val | Arg | Tyr | His | Gly | Gly |
| 16> | Asp | Glu | Ile | Ile | Leu | Gln | Gly | Phe | His | Trp | Asn | Val | Val | Arg | Glu |
| 31> | Ala | Pro | Asn | Asp | Trp | Tyr | Asn | Ile | Leu | Arg | Gln | Gln | Ala | Ala | Thr |

TABLE 4-continued

```
46>  Ile-Ala-Ala-Asp-Gly-Phe-Ser-Ala-Ile-Trp-Met-Pro-Val-Pro-Trp-
61>  Arg-Asp-Phe-Ser-Ser-Trp-Ser-Asp-Gly-Ser-Lys-Ser-Gly-Gly-Gly-
76>  Glu-Gly-Tyr-Phe-Trp-His-Asp-Phe-Asn-Lys-Asn-Gly-Arg-Tyr-Gly-
91>  Ser-Asp-Ala-Gln-Leu-Arg-Gln-Ala-Ala-Ser-Ala-Leu-Gly-Gly-Ala-
106> Gly-Val-Lys-Val-Leu-Tyr-Asp-Val-Val-Pro-Asn-His-Met-Asn-Arg-
121> Gly-Tyr-Pro-Asp-Lys-Glu-Ile-Asn-Leu-Pro-Ala-Gly-Gln-Gly-Phe-
136> Trp-Arg-Asn-Asp-Cys-Ala-Asp-Pro-Gly-Asn-Tyr-Pro-Asn-Asp-Cys-
151> Asp-Asp-Gly-Asp-Arg-Phe-Ile-Gly-Gly-Asp-Ala-Asp-Leu-Asn-Thr-
166> Gly-His-Pro-Gln-Val-Tyr-Gly-Met-Phe-Arg-Asp-Glu-Phe-Thr-Asn-
181> Leu-Arg-Ser-Gln-Tyr-Gly-Ala-Gly-Gly-Phe-Arg-Phe-Asp-Phe-Val-
196> Arg-Gly-Tyr-Ala-Pro-Glu-Arg-Val-Asn-Ser-Trp-Met-Thr-Asp-Ser-
211> Ala-Asp-Asn-Ser-Phe-Cys-Val-Gly-Glu-Leu-Trp-Lys-Gly-Pro-Ser-
226> Glu-Tyr-Pro-Asn-Trp-Asp-Trp-Arg-Asn-Thr-Ala-Ser-Trp-Gln-Gln-
241> Ile-Ile-Lys-Asp-Trp-Ser-Asp-Arg-Ala-Lys-Cys-Pro-Val-Phe-Asp-
256> Phe-Ala-Leu-Lys-Glu-Arg-Met-Gln-Asn-Ala-Arg-Ser-Pro-Thr-Gly-
271> Ser-Thr-Pro-Glu-Arg-Gln-Ser-Arg-Pro-Ala-Trp-Arg-Glu-Val-Ala-
286> Val-Thr-Phe-Val-Asp-Asn-His-Asp-Thr-Gly-Tyr-Ser-Pro-Gly-Gln-
301> Asn-Gly-Gly-Gln-His-His-Trp-Ala-Leu-Gln-Asp-Gly-Leu-Ile-Arg-
316> Gln-Ala-Tyr-Ala-Tyr-Ile-Leu-Thr-Ser-Pro-Gly-Thr-Pro-Val-Val-
331> Tyr-Trp-Ser-His-Met-Tyr-Asp-Trp-Gly-Tyr-Gly-Asp-Phe-Ile-Arg-
346> Gln-Leu-Ile-Gln-Val-Arg-Arg-Ala-Ala-Gly-Val-Arg-Ala-Asp-Ser-
361> Ala-Ile-Ser-Phe-His-Ser-Gly-Tyr-Ser-Gly-Leu-Val-Ala-Thr-Val-
376> Ser-Gly-Ser-Gln-Thr-Leu-Val-Val-Ala-Leu-Asn-Ser-Asp-Leu-
391> Gly-Asn-Pro-Gly-Gln-Val-Ala-Ser-Gly-Ser-Phe-Ser-Glu-Ala-Val-
406> Asn-Ala-Ser-Asn-Gly-Gln-Val-Arg-Val-Trp-Arg-Ser-Gly-Thr-Gly-
421> Ser-Gly-Gly-Gly-Glu-Pro-Gly-Ala
```

These amino acid sequences were compared with those of several α-amylases described in *Applied Microbiology and Biotechnology*, Vol. 23, pp. 335–360 (1986).

It was unexpectedly elucidated that polypeptide in the present invention belonging to an exo-type starch degrading enzyme had the partial amino acid sequences which had been specified as the first- to fourth-regions in an amino acid sequence of an α-amylase belonging to an endo-type starch degrading enzyme.

The results were as shown in Table 5.

TABLE 5

| Origin | (a) | (b) | (c) | (d) |
|---|---|---|---|---|
| Pseudomonas stutzeri | Asp-Val-Val-Pro-Asn-His-Met | Arg-Phe-Asp-Phe-Val-Arg-Gly-Tyr | Phe-Cys-Val-Gly-Glu-Leu-Trp-Lys-Gly | Thr-Phe-Val-Asp-Asn-His-Asp-Thr |
| Bacillus stearothermophilus | Asp-Val-Val-Phe-Asp-His-Lys | Arg-Leu-Asp-Ala-Val-Lys-His-Ile | Phe-Thr-Val-Gly-Glu-Tyr-Trp-Ser-Tyr | Thr-Phe-Val-Asp-Asn-His-Asp-Thr |
| Bacillus amyloliquefaciens | Asp-Val-Val-Leu-Asn-His-Lys | Arg-Ile-Asp-Ala-Ala-Lys-His-Ile | Phe-Thr-Val-Ala-Glu-Tyr-Trp-Gln-Asn | Thr-Phe-Val-Glu-Asn-His-Asp-Thr |
| Bacillus subtilis | Asp-Ala-Val-Ile-Asn-His-Thr | Arg-Phe-Asp-Ala-Ala-Lys-His-Ile | Phe-Gln-Tyr-Gly-Glu-Ile-Leu-Gln-Asp | Thr-Trp-Val-Glu-Ser-His-Asp-Thr |
| Aspergillus oryzae | Asp-Val-Val-Ala-Asn-His-Met | Arg-Ile-Asp-Thr-Val-Lys-His-Val | Tyr-Cys-Ile-Gly-Glu-Val-Leu-Asp-Gly | Thr-Phe-Val-Glu-Asn-His-Asp-Asn |
| Rat | Asp-Ala-Val-Ile-Asn-His-Met | Arg-Leu-Asp-Ala-Ala-Lys-His-Met | Phe-Ile-Phe-Gln-Glu-Val-Ile-Asp-Leu | Val-Phe-Val-Asp-Asn-His-Asp-Asn |
| Mouse | Asp-Ala-Val-Ile-Asn-His-Met | Arg-Leu-Asp-Ala-Ser-Lys-His-Met | Phe-Ile-Phe-Gln-Glu-Val-Ile-Asp-Leu | Val-Phe-Val-Asp-Asn-His-Asp-Asn |
| Mouse | Asp-Ala-Val-Ile-Asn-His-Met | Arg-Leu-Asp-Ala-Ala-Lys-His-Met | Phe-Ile-Phe-Gln-Glu-Val-Ile-Asp-Leu | Val-Phe-Val-Asp-Asn-His-Asp-Asn |
| Pig | Asp-Ala-Val-Ile-Asn-His-Met | Arg-Ile-Asp-Ala-Ser-Lys-His-Met | Phe-Ile-Phe-Gln-Glu-Val-Ile-Asp-Leu | Val-Phe-Val-Asp-Asn-His-Asp-Asn |
| Human | Asp-Ala-Val-Ile-Asn-His-Met | Arg-Ile-Asp-Ala-Ser-Lys-His-Met | Phe-Ile-Tyr-Gln-Glu-Val-Ile-Asp-Leu | Val-Phe-Val-Asp-Asn-His-Asp-Asn |
| Human | Asp-Ala-Val-Ile-Asn-His-Met | Arg-Leu-Asp-Ala-Ser-Lys-His-Met | Phe-Ile-Tyr-Gln-Glu-Val-Ile-Asp-Leu | Val-Phe-Val-Asp-Asn-His-Asp-Asn |
| Barley | Asp-Ile-Val-Ile-Asn-His-Arg | Arg-Leu-Asp-Phe-Ala-Arg-Gly-Tyr | Leu-Ala-Val-Ala-Glu-Val-Trp-Asp-Asn | Thr-Phe-Val-Asp-Asn-His-Asp-Thr |

As evident from the results in Table 5, it is estimated that the polypeptide in the present invention possesses partial amino acid sequences which are similar to the specific amino acid sequences of α-amylases, and the partial amino acid sequences have a great significance when acting on starch.

It was elucidated that the polypeptide in the present invention has partial amino acid sequences of (a) Asp-Val-Val-Pro-Asn-His-Met, (b) Arg-Phe-Asp-Phe-Val-Arg-Gly-Tyr, (c) Phe-Cys-Val-Gly-Glu-Leu-Trp-Lys-Gly, and (d) Thr-Phe-Val-Asp-Asn-His-Asp-Thr, and these partial amino acid sequences are located in this order with respect to the N-terminal of the polypeptide.

Several embodiments and effects of the present invention will hereinafter be explained.

EXAMPLE 1

Polypeptide

A liquid culture medium containing 3 w/v % soluble starch, 0.5 w/v % corn steep liquor, 0.2 w/v % polypeptone, 0.2 w/v % dipotassium hydrogen phosphate, 0.05 w/v % calcium chloride dihydrate and water was adjusted to pH 7.2. One hundred milliliter aliquots of the liquid culture medium were placed in 500 ml-shake-flasks, and autoclaved at 120° C. for 20 minutes. A seed culture of *Pseudomonas stutzeri* MO-19 was inoculated to each aliquot of the liquid culture medium, and cultured at 27° C. for 96 hours under shaking conditions.

The maltotetraose-forming amylase activity in the resultant culture was about 250 units/ml.

A supernatant containing polypeptide obtained by centrifugal separation of the culture can be advantageously used to prepare a high maltotetraose from amylaceous substances.

EXAMPLE 2

Polypeptide

Fifteen liters of a liquid culture medium containing 4 w/v % liquefied starch, 1.0 w/v % corn steep liquor, 0.5 w/v % polypeptone, 0.2 w/v % ammonium nitrate, 0.2 w/v % dipotassium hydrogen phosphate, 0.05 w/v % calcium chloride dihydrate and water was placed in a 30-liter jar fermentor, adjusted to pH 7.0, autoclaved at 120° C. for 20 minutes, and cooled. The liquid culture medium was added with 50 μg/ml of ampicillin, and 1 v/v % of a seed culture of *Escherichia coli* TPS618 was inoculated to the liquid culture medium, and cultured at 37° C. for 24 hours under agitation-aeration conditions. The activity of maltotetraose-forming amylase in the resultant culture was about 300 units/ml. A cell obtained from the resultant culture was subjected to ultrasonic and centrifugation to obtain a supernatant. The supernatant was then purified by the method in Experiment 2-(1) to obtain a solution containing high-purity polypeptide.

The solution containing polypeptide can be advantageously used in a preparation of a high maltotetraose from amylaceous substances.

EXAMPLE 3

High Maltotetraose

One part by weight of corn starch was admixed with 3.0 parts by weight of water containing 0.1 w/w % "Termamyl 60L®", an α-amylase commercialized by Novo industry A/S, Copenhagen, Denmark, per starch while stirring. The mixture was adjusted to pH 6.5, and allowed to stand at 95–100° C. to gelatinize and liquefy the corn starch simultaneously. Immediately after the DE of the reaction mixture reached 4.5, the resultant was heated at 120° C. for 5 minutes, and then quickly cooled to 60° C. The cooled product was then added with 4 units/g starch of a supernatant containing polypeptide obtained by the method in Example 1, and kept at pH 6.5 and 55° C. for 46 hours to effect saccharification.

The resultant saccharified product was heated to inactivate the maltotetraose-forming amylase, filtered, decolored with activated charcoal, and deionized with ion exchange resins in H- and OH-form to obtain a high maltotetraose syrup with a moisture content of 25 w/w % in the yield of 95%, d.s.b., against the material starch.

The product containing about 55% maltotetraose, d.s.b., had about 25% sweetening power of sucrose.

The product can be extensively used in food products as a sweetener with a moderate sweetness, a low saccharide content and an excellent assimilability, as well as a body-imparting agent, viscosity-controlling agent, humectant, gloss-imparting agent, adhesive, flavor-retaining agent, crystallization-preventing agent, and sticking-preventing agent for candy.

EXAMPLE 4

High Maltotetraose

One part by weight of potato starch was admixed with 6 parts by weight of water containing 0.01 w/w % "Neo-Spitase", an α-amylase commercialized by Nagase Biochemicals, Ltd., Kyoto, Japan, per starch while stirring. The mixture was adjusted to pH 6.0, and heated at 85–90° C. to gelatinize and liquefy the starch. The resultant mixture was immediately heated to 120° C. within 5 minutes in order to retain its DE to a level lower than 1.0, quickly cooled to 55° C., and adjusted to pH 7.0. To the reaction mixture was added "pullulanase (EC 3.2.1.41)", a product of Hayashibara Biochemical Laboratories Inc., Okayama, Japan, and a high-purity polypeptide solution, obtained by the method in Example 2, in respective amount of 150 units/g starch and 8 units/g starch, and the resultant was kept at pH 7.0 and 50° C. for 36 hours to effect saccharification.

The resultant saccharified product was purified and concentrated similarly as in Example 3, and then spray-dried to obtain a powder with a moisture content lower than 1 w/w %. The yield was about 93%, d.s.b., against the material starch.

The product containing about 76% maltotetraose, d.s.b., had 25% sweetening power of sucrose.

Similarly as the product in Example 3, this product can be extensively used in food products as a sweetener with a moderate sweetness, a low saccharide content and an excellent assimilability.

EXAMPLE 5

High Maltotetraose

The maltotetraose content of a product obtained by the method in Example 4 was increased by using a strongly-acidic cation exchange resin.

A product obtained by the method in Example 4 was dissolved to give a concentration of 60 w/w %, and then used as a feed solution. "XT-1007 (in alkaline metal form)", a strongly-acidic cation exchange resin commercialized by Tokyo Chemical Industries, Kita-ku, Tokyo, Japan, was packed in 4 jacketted stainless steel columns, 5.4 cm in diameter, and the columns were cascaded to give a total bed depth of 20 m. The feed solution was admitted to the columns in an amount of 5 v/v % against the resin, and 55° C. water was passed through the columns at a space velocity (SV) of 0.13 to effect fractionation, followed by recovery of the fractions containing 90% or more maltotetraose. The fractions were purified and concentrated similarly as in Example 3 to obtain a syrup with a moisture content of 25 w/w % in the yield of about 60%, d.s.b., against the material saccharide.

The product containing about 93% maltotetraose, d.s.b., had about 25% sweetening power of sucrose.

Similarly as the product in Example 3, the product can be extensively used in food products as a sweetener with a moderate sweetness, a low saccharide content and an excellent assimilability.

EXAMPLE 6
High Maltotetraitol

A product obtained by the method in Example 3 was prepared into a 50% aqueous solution. The aqueous solution was placed in an autoclave, added with 10% Raney Nickel as the catalyst, and heated to 90–125° C. under a hydrogen pressure of 20–100 kg/cm$^2$ to complete hydrogenation while stirring. The Raney Nickel was removed from the reaction mixture, and the residue was purified and concentrated similarly as in Example 3 to obtain a high maltotetraitol syrup with a moisture content of 25 w/w % in the yield of about 92%, d.s.b., against the material high maltotetraose.

The product containing about 55% maltotetraitol, d.s.b., had about 30% sweetening power of sucrose. The product can be extensively used in food products as a sweetener with a moderate sweetness but without reducing ability, as well as a body-imparting agent, viscosity-controlling agent, humectant, gloss-imparting agent, adhesive, flavor-retaining agent, crystallization-preventing agent and sticking-preventing agent for candy.

EXAMPLE 7
High Maltotetraitol

A product obtained by the method in Example 4 was hydrogenated, purified and concentrated by the method in Example 6 to obtain a high maltotetraitol with a moisture content of about 25 w/w % in the yield of about 92%, d.s.b., against the material high maltotetraose.

The product containing about 76% maltotetraitol, d.s.b., had about 30% sweetening power of sucrose.

Similarly as the product in Example 6, the product can be extensively used in food products as a sweetener with a moderate sweetness but without reducing ability.

EXAMPLE 8
Sweetener

One part by weight of a syrup obtained by the method in Example 5 was mixed homogeneously with 0.02 parts by weight of "α-G-Sweet®", α-glycosyl stevioside syrup commercialized by Toyo Sugar Refining Co., Ltd., Tokyo, Japan, to obtain a syrup sweetener. The syrup sweetener with an excellent sweetness has an about 2-fold stronger sweetening power of sucrose, and its calorie is about one-half of sucrose with respect to the sweetening power. Thus, the syrup sweetener can be favorably used to sweeten low-caloric food products for those whose calorie intakes are restricted such as obeses and diabetics.

The syrup sweetener can be favorably used to sweeten dental caries-preventing food products because it induces less formation of acid and insoluble glucan by a dental cariesinducing microorganism.

EXAMPLE 9
Custard Cream

Five hundred parts by weight of corn starch, 400 parts by weight of a powder obtained by the method in Example 4,500 parts by weight of maltose, and 5 parts by weight of table salt were homogeneously mixed through mesh. The mixture was added with 1,400 parts by weight of egg, stirred and slowly added with 5,000 parts by weight of boiling milk. Thereafter, the resultant was stirred while heating with a slow fire, and the heating was stopped when the corn starch was completely gelatinized and became entirely semi-permeable. The product was cooled and added with a small amount of vanilla flavor to obtain a custard cream.

The product has a smooth texture, excellent gloss and moderate sweetness.

EXAMPLE 10
"Uiro (a sweet rice jelly)"

Ninety parts by weight of rice powder was kneaded with 20 parts by weight of corn starch, 20 parts by weight of sugar, 1 part by weight of "maccha (a powdered green tea)", 90 parts by weight of a syrup obtained by the method in Example 7, and an appropriate amount of water. The mixture was placed in a vessel, and steamed for 60 minutes to obtain "uiro".

The product was excellent in gloss, biting properties, flavor and taste. The product was stable over a long period of time because retrogradation of its amylaceous constituent was suppressed.

EXAMPLE 11
Hard Candy

Ninety parts by weight of sucrose was dissolved in 70 parts by weight of a syrup obtained by the method in Example 5, and the mixture was concentrated in vacuo to give a moisture content below about 2 w/w % while heating. The resultant was mixed with 0.15 parts by weight of citric acid and small amounts of flavors including lemon flavor. The resultant was then shaped in conventional manner to obtain a hard candy.

The hard candy is appropriately crisp because it effects less moisture adsorption and scarcely causes sticking.

EXAMPLE 12
"Tsukudani (foods boiled down in soy)"

Two hundred and fifty parts by weight of tangle which had been treated to remove the sand adhering thereto, soaked in acid solution and cut into squares in conventional manner was added with 212 parts by weight of soy source, 300 parts by weight of amino acid solution, 40 parts by weight of sugar, and 20 parts by weight of a syrup obtained by the method in Example 3. Then, the mixture was added with 12 parts by weight of sodium glutamic acid, 8 parts by weight of caramel and 21 parts by weight of "mirin" while boiling, and the resultant was boiled down to obtain "konbu-no-tsukudani (a tsukudani of tangle)".

The product is an appetizing "konbu-no-tsukudani" with an excellent color, gloss, taste and flavor.

EXAMPLE 13
"Bettara-zuke (a kind of whole fresh radish pickles)"

Four parts by weight of a syrup sweetener obtained by the method in Example 8, 0.05 parts by weight of licorice preparation, 0.008 parts by weight of malic acid, 0.07 parts by weight of sodium glutamate, 0.03 parts by weight of potassium sorbinate, and 0.2 parts by weight of pullulan were homogeneously mixed to obtain "bettara-zuke-no-moto (a premix for bettara-zuke)".

Thirty kilograms of Japanese radish was pickled with following salt, sugar and a solution prepared by using 4 kg of "bettarzuke-no-moto" to obtain "bettara-zuke".

The product was moderately sweet and excellent in biting properties, color, gloss and flavor.

EXAMPLE 14
Fluid Food for Intubation Feeding

A composition was prepared with following: 550 parts by weight of a powder obtained by the method in Example 4; 50 parts by weight of "FINETOSEO®", an anhydrous crystalline α-maltose commercialized by Hayashibara Co., Ltd., Okayama, Japan; 190 parts by weight of dried egg-yolk; 209 parts by weight of skim milk powder; 4.4 parts by weight of sodium chloride; 1.85 parts by weight of potassium chloride; 4 parts by weight of manganese sulphate; 0.01 part by weight of thiamine; 0.1 part by weight of ascorbic acid; 0.6 parts by weight of vitamin E acetate; and 0.04 parts by weight of nicotinamide.

Twenty-five gram aliquots of the composition were packaged in laminated aluminum bags, and the bags were heat-sealed to obtain a solid nutrient supplement.

The product excellent in free-flowing ability, solubility and dispersibility requires no low-temperature storage because it is stable even at ambient temperature over a long period of time.

A fluid food prepared by dissolving one bag of the product in about 150–300 ml of water can be administered through nasal cavity, esophagus, stomach or intestine by means of intubation feeding.

EXAMPLE 15
Tablet

Fifty parts by weight of salicylic acid was homogeneously mixed with 6 parts by weight of a powder obtained by the method in Example 4, and 8 parts by weight of corn starch, and the mixture was tabletted with a tablet machine to obtain a tablet with 5.25 mm in thickness and 680 mg in weight.

The tablet had a relatively low hygroscopicity, a sufficient physical strength, and an excellent degradability in water.

EFFECT OF THE INVENTION

As evident from the above, the present invention relates to an elucidation of amino acid sequences of a polypeptide, a process for preparing a high maltotetraose from amylaceous substances using the polypeptide and a process for preparing a high maltotetraitol from the high maltotetraose. Furthermore, the present invention relates to a process for preparing food products using those high maltotetraose and high maltotetraitol.

The present inventors have elucidated that polypeptide which possesses the specific amino acid sequences can safely hydrolyze starch and facilitate a process for preparing food products with an excellent flavor and taste by using the hydrolysates and their hydrogenated substances. Thus, the polypeptide has a great significance in industrial uses.

Furthermore, it is also a great feature that the polypeptide which has been incorporated in amylaceous substances does not spoil flavor and taste of food products, and the food products can be safely tasted without further processings.

The present inventors have elucidated that a microorganism of the species *Pseudomonas stutzeri* which possesses polypeptide producibility, as well as that a transformed microorganism in which the polypeptide gene has been introduced by genetic engineering technique in vitro, can be used as a polypeptide producer. The elucidation has a great significance in industrial uses because the present invention can ensure the wide variety of polypeptide producers, as well as facilitating the improvement of the polypeptide producibility.

While there has been described what is at present considered to be preferred embodiments of the invention, it will be understood that various modifications may be made therein, and it is intended to cover in the appended claims all such modifications as fall within the true spirits and scope of the invention.

We claim:

1. Isolated DNA comprising DNA having a nucleotide sequence coding for a polypeptide possessing maltotetraose-forming amylase activity having the following partial amino acid sequences:

(a) Asp-Val-Val-Pro-Asn-His-Met, (b) Arg-Phe-Asp-Phe-Val-Arg-Gly-Tyr, (c) Phe-Cys-Val-Gly-Glu-Leu-Trp-Lys-Gly, and (d) Thr-Phe-Val-Asp-Asn-His-Asp-Thr, wherein, in the polypeptide which the DNA encodes, partial sequence (a) is closest to the N-terminal of the polypeptide, partial sequence (b) is farther from the N-terminal of the polypeptide than partial sequence (a), partial sequence (c) is farther from the N-terminal of the polypeptide than partial sequence (b), and partial sequence (d) is farther from the N-terminal of the polypeptide than partial sequence (c).

2. DNA in accordance with claim 1, wherein the polypeptide which the DNA encodes includes the following N-terminal sequence:

Asp-Gln-Ala-Gly-Lys-Ser-Pro-Asn-Ala-Val-Arg-Tyr-His-Gly-Gly-Asp-Glu-Ile-Ile-Leu.

3. DNA in accordance with claim 2, wherein the polypeptide which the DNA encodes has the following amino acid sequence:

```
         1   2   3   4   5   6   7   8   9   10  11  12  13  14  15
  1> Asp-Gln-Ala-Gly-Lys-Ser-Pro-Asn-Ala-Val-Arg-Tyr-His-Gly-Gly-

16> Asp-Glu-Ile-Ile-Leu-Gln-Gly-Phe-His-Trp-Asn-Val-Val-Arg-Glu-

31> Ala-Pro-Asn-Asp-Trp-Tyr-Asn-Ile-Leu-Arg-Gln-Gln-Ala-Ala-Thr-

46> Ile-Ala-Ala-Asp-Gly-Phe-Ser-Ala-Ile-Trp-Met-Pro-Val-Pro-Trp-

61> Arg-Asp-Phe-Ser-Ser-Trp-Ser-Asp-Gly-Ser-Lys-Ser-Gly-Gly-Gly-

76> Glu-Gly-Tyr-Phe-Trp-His-Asp-Phe-Asn-Lys-Asn-Gly-Arg-Tyr-Gly-

91> Ser-Asp-Ala-Gln-Leu-Arg-Gln-Ala-Ala-Ser-Ala-Leu-Gly-Gly-Ala-

106> Gly-Val-Lys-Val-Leu-Tyr-Asp-Val-Val-Pro-Asn-His-Met-Asn-Arg-

121> Gly-Tyr-Pro-Asp-Lys-Glu-Ile-Asn-Leu-Pro-Ala-Gly-Gln-Gly-Phe-
```

-continued

```
136> Trp-Arg-Asn-Asp-Cys-Ala-Asp-Pro-Gly-Asn-Tyr-Pro-Asn-Asp-Cys-

151> Asp-Asp-Gly-Asp-Arg-Phe-Ile-Gly-Gly-Asp-Ala-Asp-Leu-Asn-Thr-

166> Gly-His-Pro-Gln-Val-Tyr-Gly-Met-Phe-Arg-Asp-Glu-Phe-Thr-Asn-

181> Leu-Arg-Ser-Gln-Tyr-Gly-Ala-Gly-Gly-Phe-Arg-Phe-Asp-Phe-Val-

196> Arg-Gly-Tyr-Ala-Pro-Glu-Arg-Val-Asn-Ser-Trp-Met-Thr-Asp-Ser-

211> Ala-Asp-Asn-Ser-Phe-Cys-Val-Gly-Glu-Leu-Trp-Lys-Gly-Pro-Ser-

226> Glu-Tyr-Pro-Asn-Trp-Asp-Trp-Arg-Asn-Thr-Ala-Ser-Trp-Gln-Gln-

241> Ile-Ile-Lys-Asp-Trp-Ser-Asp-Arg-Ala-Lys-Cys-Pro-Val-Phe-Asp-

256> Phe-Ala-Leu-Lys-Glu-Arg-Met-Gln-Asn-Ala-Arg-Ser-Pro-Thr-Gly-

271> Ser-Thr-Pro-Glu-Arg-Gln-Ser-Arg-Pro-Ala-Trp-Arg-Glu-Val-Ala-

286> Val-Thr-Phe-Val-Asp-Asn-His-Asp-Thr-Gly-Tyr-Ser-Pro-Gly-Gln-

301> Asn-Gly-Gly-Gln-His-His-Trp-Ala-Leu-Gln-Asp-Gly-Leu-Ile-Arg-

316> Gln-Ala-Tyr-Ala-Tyr-Ile-Leu-Thr-Ser-Pro-Gly-Thr-Pro-Val-Val-

331> Tyr-Trp-Ser-His-Met-Tyr-Asp-Trp-Gly-Tyr-Gly-Asp-Phe-Ile-Arg-

346> Gln-Leu-Ile-Gln-Val-Arg-Arg-Ala-Ala-Gly-Val-Arg-Ala-Asp-Ser-

361> Ala-Ile-Ser-Phe-His-Ser-Gly-Tyr-Ser-Gly-Leu-Val-Ala-Thr-Val-

376> Ser-Gly-Ser-Gln-Gln-Thr-Leu-Val-Val-Ala-Leu-Asn-Ser-Asp-Leu-

391> Gly-Asn-Pro-Gly-Gln-Val-Ala-Ser-Gly-Ser-Phe-Ser-Glu-Ala-Val-

406> Asn-Ala-Ser-Asn-Gly-Gln-Val-Arg-Val-Trp-Arg-Ser-Gly-Thr-Gly-

421> Ser-Gly-Gly-Gly-Glu-Pro-Gly-Ala-Leu-Val-Ser-Val-Ser-Phe-Arg-

436> Cys-Asp-Asn-Gly-Ala-Thr-Gln-Met-Gly-Asp-Ser-Val-Tyr-Ala-Val-

451> Gly-Asn-Val-Ser-Gln-Leu-Gly-Asn-Trp-Ser-Pro-Ala-Ala-Ala-Leu-

466> Arg-Leu-Thr-Asp-Thr-Ser-Gly-Tyr-Pro-Thr-Trp-Lys-Gly-Ser-Ile-

481> Ala-Leu-Pro-Ala-Gly-Gln-Asn-Glu-Glu-Trp-Lys-Cys-Leu-Ile-Arg-

496> Asn-Glu-Ala-Asn-Ala-Thr-Gln-Val-Arg-Gln-Trp-Gln-Gly-Gly-Ala-

511> Asn-Asn-Ser-Leu-Thr-Pro-Ser-Glu-Gly-Ala-Thr-Thr-Val-Gly-Arg-

526> Leu.
```

4. A vector including the DNA in accordance with claim 1.

5. A vector including the DNA in accordance with claim 2.

6. A vector including the DNA in accordance with claim 3.

7. A vector including the DNA in accordance with claim 6.

8. A transformed cell consisting of a cell of a microorganism which is not naturally capable of producing α-amylase, which cell has been transformed to include the DNA in accordance with claim 1, or progeny of said cell, which progeny contains said DNA, where said cell and said progeny produce the protein encoded by said DNA.

9. A transformed cell consisting of a cell of a microorganism which is not naturally capable of producing α-amylase, which cell has been transformed to include the DNA in accordance with claim 3, or progeny of said cell, which progeny contains said DNA, wherein said cell and said progeny produce the protein encoded by said DNA.

10. A transformed cell consisting of a cell of a microorganism which is not naturally capable of producing α-amylase, which cell has been transformed to include the DNA in accordance with claim 4, or progeny of said cell, which progeny contains said DNA, wherein said cell and said progeny produce the protein encoded by said DNA.

11. A transformed cell consisting of a cell of a microorganism which is not naturally capable of producing α-amylase, which cell has been transformed to include the DNA in accordance with claim 7, or progeny of said cell, which progeny contains said DNA, wherein said cell and said progeny produce the protein encoded by said DNA.

12. A method of producing pure, stable polypeptide possessing maltotetraose-forming amylase activity, comprising:
  incubating a cell in accordance with claim 8 under conditions such that the polypeptide is expressed; and
  recovering and purifying the polypeptide.

13. A method of producing pure, stable polypeptide possessing maltotetraose-forming amylase activity, comprising:
  incubating a cell in accordance with claim 9 under conditions such that the polypeptide is expressed; and
  recovering and purifying the polypeptide.

14. A method of producing pure, stable polypeptide possessing maltotetraose-forming amylase activity, comprising:

incubating a cell in accordance with claim 10 under conditions such that the polypeptide is expressed; and recovering and purifying the polypeptide.

15. A method of producing pure, stable polypeptide possessing maltotetraose-forming amylase activity, comprising:

incubating a cell in accordance with claim 11 under conditions such that the polypeptide is expressed; and recovering and purifying the polypeptide.

16. Isolated DNA coding for a polypeptide possessing maltotetraose-forming amylase activity, comprising DNA having the following sequence:

```
          10         20         30         40         50         60
  GATCAGGCCG GCAAGAGCCC CAACGCTGTG CGCTACCACG GCGGCGACGA AATCATTCTC 70         80         90        100        110        120
  CAGGGCTTTC ACTGGAACGT CGTCCGCGAA GCGCCCAACG ACTGGTACAA CATCCTGCGC 130        140        150        160        170        180
  CAGCAGGCCG CGACCATCGC CGCCGACGGC TTCTCGGCGA TCTGGATGCC GGTGCCCTGG 190        200        210        220        230        240
  CGCGACTTCT CCAGCTGGAG CGACGGCAGC AAGTCCGGCG GCGGTGAAGG CTACTTCTGG 250        260        270        280        290        300
  CACGACTTCA ACAAGAACGG CCGCTATGGC AGTGACGCCC AGCTGCGTCA GGCCGCCAGC 310        320        330        340        350        360
  GCGCTCGGTG GCGCCGGCGT GAAAGTGCTT TACGACGTGG TGCCCAACCA CATGAACCGT 370        380        390        400        410        420
  GGCTATCCGG ACAAGGAGAT CAACCTCCCG GCCGGCCAGG GCTTCTGGCG CAACGACTGC 430        440        450        460        470        480
  GCCGACCCGG GCAACTACCC CAATGATTGC GACGACGGCG ACCGCTTCAT CGGCGGCGAT 490        500        510        520        530        540
  GCGGACCTCA ACACCGGCCA CCCGCAGGTC TACGGCATGT TCCGCGATGA ATTCACCAAC 550        560        570        580        590        600
  CTGCGCAGTC AGTACGGTGC CGGCGGCTTC CGCTTCGACT TTGTTCGGGG CTATGCGCCG 610        620        630        640        650        660
  GAGCGGGTCA ACAGCTGGAT GACCGATAGC GCCGACAACA GCTTCTGCGT CGGCGAACTG 670        680        690        700        710        720
  TGGAAAGGCC CCTCTGAGTA CCCGAACTGG GACTGGCGCA ACACCGCCAG CTGGCAGCAG 730        740        750        760        770        780
  ATCATCAAGG ACTGGTCCGA CCGGGCCAAG TGCCCGGTGT TCGACTTCGC CCTCAAGGAA 790        800        810        820        830        840
  CGCATGCAGA ACGCTCGATC GCCGACTGGA AGCACGCCTG AACGGCAATC CCGACCCGCG 850        860        870        880        890        900
  TGGCGCGAGG TGGCGGTGAC CTTGGTCGAC AACCACGACA CCGGCTACTC GCCCGGGCAG 910        920        930        940        950        960
  AACGGTGGGC AGCACCACTG GGCTCTGCAG GACGGGCTGA TCCGCCAGGC CTACGCCTAC 970        980        990       1000       1010       1020
  ATCCTCACCA GCCCCGGTAC GCCGGTGGTG TACTGGTCGC ACATGTACGA CTGGGGTTAC 1030       1040       1050       1060       1070       1080
  GGCGACTTCA TCCGTCAGCT GATCCAGGTG CGTCGCGCCG CCGGCGTGCG CGCCGATTCG 1090       1100       1110       1120       1130       1140
  GCGATCAGCT TCCACAGCGG CTACAGCGGT CTGGTCGCCA CCGTCAGCGG CAGCCAGCAG 1150       1160       1170       1180       1190       1200
  ACCCTGGTGG TGGCGCTCAA CTCCGACCTG GGCAATCCCG GCCAGGTGGC CAGCGGCAGC 1210       1220       1230       1240       1250       1260
  TTCAGCGAGG CGGTCAACGC CAGCAACGGC CAGGTGCGCG TGTGGCGTAG CGGCACGGGC 1270       1280       1290       1300       1310       1320
  AGCGGTGGCG GTGAACCCGG CGCTCTGGTC AGTGTGAGTT TCCGCTGCGA CAACGGCGCG 1330       1340       1350       1360       1370       1380
  ACGCAGATGG GCGACAGCGT CTACGCGGTC GGCAACGTCA GCCAGCTCGG TAACTGGAGC 1390       1400       1410       1420       1430       1440
  CCGGCCGCGG CGTTGCGCCT GACCGACACC AGCGGCTACC CGACCTGGAA GGGCAGCATT
```

-continued

```
        1450        1460       1470       1480       1490       1500
GCCTTGCCTG CCGGCCAGAA CGAGGAATGG AAATGCCTGA TCCGCAACGA GGCCAACGCC 1510        1520       1530       1540       1550       1560
ACCCAGGTGC GGCAATGGCA GGGCGGGGCA AACAACAGCC TGACGCCGAG CGAGGGCGCC

1570
ACCACCGTCG GCCGGCTC.
```

\* \* \* \* \*